(12) United States Patent
Robinson et al.

(10) Patent No.: US 9,689,030 B2
(45) Date of Patent: Jun. 27, 2017

(54) POLYMERASE CHAIN REACTION DETECTION SYSTEM

(71) Applicant: LGC Genomics Limited, Teddington (GB)

(72) Inventors: Philip Steven Robinson, Aylesbury (GB); John Holme, Hoddesdon (GB); Nisha Jain, Hoddesdon (GB)

(73) Assignee: LGC Genomics Limited (GB)

( * ) Notice: Subject to any disclaimer, the term of this patent is extended or adjusted under 35 U.S.C. 154(b) by 0 days.

(21) Appl. No.: 14/825,093

(22) Filed: Aug. 12, 2015

(65) Prior Publication Data

US 2015/0337365 A1     Nov. 26, 2015

Related U.S. Application Data

(62) Division of application No. 13/427,686, filed on Mar. 22, 2012, now Pat. No. 9,133,509.

(51) Int. Cl.
*C12Q 1/68* (2006.01)
*G01N 21/64* (2006.01)

(52) U.S. Cl.
CPC ......... *C12Q 1/6858* (2013.01); *C12Q 1/6853* (2013.01); *G01N 2021/6432* (2013.01)

(58) Field of Classification Search
CPC ............ C12Q 1/6853; C12Q 2525/186; C12Q 2537/137; C12Q 2537/163; C12Q 2565/101; C12Q 1/6858; G01N 2021/6432
See application file for complete search history.

(56) References Cited

U.S. PATENT DOCUMENTS

| | | | |
|---|---|---|---|
| 5,518,900 A | 5/1996 | Nikiforov et al. | |
| 5,538,848 A | 7/1996 | Livak et al. | |
| 5,716,784 A | 2/1998 | Di Cesare | |
| 5,866,336 A | 2/1999 | Nazarenko et al. | |
| 7,070,962 B1 | 7/2006 | Ryncarz | |
| 7,615,620 B2 | 11/2009 | Robinson | |
| 9,133,509 B2* | 9/2015 | Robinson | C12Q 1/6853 |
| 2003/0087271 A1* | 5/2003 | Ebersole | C12Q 1/6816 435/6.12 |
| 2003/0149257 A1 | 8/2003 | Sorge et al. | |
| 2003/0207267 A1 | 11/2003 | Lasken et al. | |
| 2003/0215826 A1 | 11/2003 | Mayrand | |
| 2005/0053972 A1 | 3/2005 | Stanton, Jr. et al. | |
| 2006/0035217 A1 | 2/2006 | Livak et al. | |
| 2009/0181366 A1 | 7/2009 | Ong et al. | |
| 2010/0041053 A1 | 2/2010 | Fiss et al. | |
| 2010/0129792 A1 | 5/2010 | Makrigiorgos | |
| 2010/0190157 A1 | 7/2010 | Adlerstein et al. | |
| 2011/0136889 A1 | 6/2011 | Bhanot et al. | |

FOREIGN PATENT DOCUMENTS

| | | |
|---|---|---|
| EP | 0744470 | 11/1996 |
| EP | 1502958 | 2/2005 |
| EP | 1726664 | 11/2006 |
| WO | WO0188195 | 11/2001 |

OTHER PUBLICATIONS

Ahern et al., The Scientist, vol. 20, pp. 1-9, Jul. 1995.*
Carlos M.G. De Noronha and James I. Mullins; "Amplimers with 3'-Terminal Phosphorothioate Linkages Resist Degradation by Vent Polymerase and Reduce Taq Polymerase Mispriming"; Nov. 1, 1992; 6 Pages.
Kai Koo and Lee-Ann Jaykus; "Detection of Listeria monocytogenes from a Model Food by Fluorescence Resonance Energy Transfer-Based PCR with an Asymmetric Fluorogenic Probe Set"; Nov. 1, 2002; 8 Pages.
Jia Zhang and Kai Li; "Single-Base Discrimination Mediated by Proofreading 3' Phosphorothioate-Modified Primers"; Jan. 1, 2003; 6 Pages.
Ya Jun Hu, Zong Fang Li and Alan M. Diamond; "Enhanced discrimination of single nucleotide polymorphism in genotyping by phosphorothioate proofreading allele-specific amplification"; Mar. 22, 2007; 6 Pages.
Yang, HL et al., "High Fidelity PCR With an Off/On Switch Mediated by Proofreading Polymerases Combining With Phosphorothioate-Modified Primer", Biochem Biophys Res Commun, Mar. 4, 2005, 1 page.
Zhang, J et al., "Proofreading Genotyping Assays Mediated by High Fidelity Exo+ DNA Polymerases", Trends Biotechnol., Feb. 2005, 1 page.
Zhang, J and Li, K, "Single-Base Discrimination Mediated by Proofreading 3' Phosphorothioate-Modified Primers", Mol Biotechnol, Nov. 2003, 1 page.
Ozaki, H et al., "Detection of DNA Bending in a DNA-PAP1 Protein Complex by Fluorescense Resonance Energy Transfer", Feb. 24, 1997, 1 page.
Nikiforov, TT et al, "The Use of Phosphorothioate Primers and Exonuclease Hydrolysis for the Preparation of Single-Stranded PCR Products and Their Detection by Solid-Phase Hybridization", Apr. 1994, 1 page.
De Noronha, CM and Mullin, JI, "Amplimers With 3'-Terminal Phosphorothioate Linkages Resist Degradation by Vent Polymerase and Reduce Taq Polymerase Mispriming", Nov. 1992, 1 page.
Okamura et al., "Double-labeled donor probe can enhance the signal of fluorescence resonance energy transfer (FRET) in detection of nucleic acid hybridization," Nucleic Acids Research , vol. 28, No. 24, e107, pp. 1-6, 2000.
Skerra., "Phosphorothioate primers improve the amplification of DNA sequences by DNA polymerases with proofreading activity," Nucleic Acid Research, vol. 20, No. 14, pp. 3551-3554, 1992.
Liang et al., Optical Antisense Tumor Targeting in Vivo with an Improved Fluorescent DNA Duplex Probe, Bioconjug. Chem. Jun. 2009, 20(6): 1223-1227.
Liu et al., Optical Antisense Imaging of Tumor with Fluorescent DNA Duplexes, Bioconjugate Chem. 2007, 18, 1905-1911.

* cited by examiner

*Primary Examiner* — Cynthia B Wilder
(74) *Attorney, Agent, or Firm* — Geoffrey M. Karny

(57) ABSTRACT

The present invention relates to methods and kits for nucleic acid detection in an assay system.

19 Claims, 16 Drawing Sheets

Direct detection of DNA sequence

SEQUENCE LISTING

```
<160> NUMBER OF SEQ ID NOS: 19

<210> SEQ ID NO 1
<211> LENGTH: 20
<212> TYPE: DNA
<213> ORGANISM: Artificial Sequence
<220> FEATURE:
<223> OTHER INFORMATION: Labelled primer

<400> SEQUENCE: 1
gcgattagcc gttaggatga                                               20

<210> SEQ ID NO 2
<211> LENGTH: 20
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (19)..(20)
<223> OTHER INFORMATION: phosphorothioate linkage

<400> SEQUENCE: 2
gcgattagcc gttaggatga                                               20

<210> SEQ ID NO 3
<211> LENGTH: 20
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (1)..(2)
<223> OTHER INFORMATION: phosphorothioate linkage
<220> FEATURE:
```

```
<221> NAME/KEY: modified_base
<222> LOCATION: (3)..(4)
<223> OTHER INFORMATION: phosphorothioate linkage
<220> FEATURE:
<221> NAME/KEY: modified_base
<222> LOCATION: (5)..(6)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (9)..(10)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (13)..(14)
<223> OTHER INFORMATION: phosphorothioate linkage
<220> FEATURE:
<221> NAME/KEY: modified_base
<222> LOCATION: (15)..(16)
<223> OTHER INFORMATION: phosphorothioate linkage
<220> FEATURE:
<221> NAME/KEY: modified_base
<222> LOCATION: (17)..(18)
<223> OTHER INFORMATION: phosphorothioate linkage
<220> FEATURE:
<221> NAME/KEY: modified_base
<222> LOCATION: (19)..(20)
<223> OTHER INFORMATION: phosphorothioate linkage

<400> SEQUENCE: 3
gcgattagcc gttaggatga                                               20

<210> SEQ ID NO 4
<211> LENGTH: 20
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (1)..(2)
<223> OTHER INFORMATION: phosphorothioate linkage
<220> FEATURE:
<221> NAME/KEY: modified_base
<222> LOCATION: (2)..(3)
<223> OTHER INFORMATION: phosphorothioate linkage
<220> FEATURE:
<221> NAME/KEY: modified_base
<222> LOCATION: (3)..(4)
<223> OTHER INFORMATION: phosphorothioate linkage
<220> FEATURE:
<221> NAME/KEY: modified_base
<222> LOCATION: (4)..(5)
<223> OTHER INFORMATION: phosphorothioate linkage
<220> FEATURE:
<221> NAME/KEY: modified_base
<222> LOCATION: (5)..(6)
<223> OTHER INFORMATION: phosphorothioate linkage
<220> FEATURE:
<221> NAME/KEY: modified_base
<222> LOCATION: (6)..(7)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (8)..(9)
<223> OTHER INFORMATION: phosphorothioate linkage
```

-continued

```
<220> FEATURE:
<221> NAME/KEY: modified_base
<222> LOCATION: (9)..(10)
<223> OTHER INFORMATION: phosphorothioate linkage
<220> FEATURE:
<221> NAME/KEY: modified_base
<222> LOCATION: (10)..(11)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (12)..(13)
<223> OTHER INFORMATION: phosphorothioate linkage
<220> FEATURE:
<221> NAME/KEY: modified_base
<222> LOCATION: (13)..(14)
<223> OTHER INFORMATION: phosphorothioate linkage
<220> FEATURE:
<221> NAME/KEY: modified_base
<222> LOCATION: (14)..(15)
<223> OTHER INFORMATION: phosphorothioate linkage
<220> FEATURE:
<221> NAME/KEY: modified_base
<222> LOCATION: (15)..(16)
<223> OTHER INFORMATION: phosphorothioate linkage
<220> FEATURE:
<221> NAME/KEY: modified_base
<222> LOCATION: (16)..(17)
<223> OTHER INFORMATION: phosphorothioate linkage
<220> FEATURE:
<221> NAME/KEY: modified_base
<222> LOCATION: (17)..(18)
<223> OTHER INFORMATION: phosphorothioate linkage
<220> FEATURE:
<221> NAME/KEY: modified_base
<222> LOCATION: (18)..(19)
<223> OTHER INFORMATION: phosphorothioate linkage
<220> FEATURE:
<221> NAME/KEY: modified_base
<222> LOCATION: (19)..(20)
<223> OTHER INFORMATION: phosphorothioate linkage

<400> SEQUENCE: 4
gcgattagcc gttaggatga                                          20

<210> SEQ ID NO 5
<211> LENGTH: 20
<212> TYPE: DNA
<213> ORGANISM: Artificial Sequence
<220> FEATURE:
<223> OTHER INFORMATION: Labelled primer

<400> SEQUENCE: 5
gtcggtgaac aggttagaga                                          20

<210> SEQ ID NO 6
<211> LENGTH: 20
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (19)..(20)
<223> OTHER INFORMATION: phosphorothioate linkage

<400> SEQUENCE: 6
gtcggtgaac aggttagaga                                          20

<210> SEQ ID NO 7
```

```
<211> LENGTH: 20
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (1)..(2)
<223> OTHER INFORMATION: phosphorothioate linkage
<220> FEATURE:
<221> NAME/KEY: modified_base
<222> LOCATION: (3)..(4)
<223> OTHER INFORMATION: phosphorothioate linkage
<220> FEATURE:
<221> NAME/KEY: modified_base
<222> LOCATION: (5)..(6)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (9)..(10)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (13)..(14)
<223> OTHER INFORMATION: phosphorothioate linkage
<220> FEATURE:
<221> NAME/KEY: modified_base
<222> LOCATION: (15)..(16)
<223> OTHER INFORMATION: phosphorothioate linkage
<220> FEATURE:
<221> NAME/KEY: modified_base
<222> LOCATION: (17)..(18)
<223> OTHER INFORMATION: phosphorothioate linkage
<220> FEATURE:
<221> NAME/KEY: modified_base
<222> LOCATION: (19)..(20)
<223> OTHER INFORMATION: phosphorothioate linkage

<400> SEQUENCE: 7
gtcggtgaac aggttagaga                                         20

<210> SEQ ID NO 8
<211> LENGTH: 20
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (1)..(2)
<223> OTHER INFORMATION: phosphorothioate linkage
<220> FEATURE:
<221> NAME/KEY: modified_base
<222> LOCATION: (2)..(3)
<223> OTHER INFORMATION: phosphorothioate linkage
<220> FEATURE:
<221> NAME/KEY: modified_base
<222> LOCATION: (3)..(4)
<223> OTHER INFORMATION: phosphorothioate linkage
<220> FEATURE:
<221> NAME/KEY: modified_base
<222> LOCATION: (4)..(5)
<223> OTHER INFORMATION: phosphorothioate linkage
<220> FEATURE:
<221> NAME/KEY: modified_base
<222> LOCATION: (5)..(6)
<223> OTHER INFORMATION: phosphorothioate linkage
<220> FEATURE:
<221> NAME/KEY: modified_base
```

<222> LOCATION: (6)..(7)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (8)..(9)
<223> OTHER INFORMATION: phosphorothioate linkage
<220> FEATURE:
<221> NAME/KEY: modified_base
<222> LOCATION: (9)..(10)
<223> OTHER INFORMATION: phosphorothioate linkage
<220> FEATURE:
<221> NAME/KEY: modified_base
<222> LOCATION: (10)..(11)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (12)..(13)
<223> OTHER INFORMATION: phosphorothioate linkage
<220> FEATURE:
<221> NAME/KEY: modified_base
<222> LOCATION: (13)..(14)
<223> OTHER INFORMATION: phosphorothioate linkage
<220> FEATURE:
<221> NAME/KEY: modified_base
<222> LOCATION: (14)..(15)
<223> OTHER INFORMATION: phosphorothioate linkage
<220> FEATURE:
<221> NAME/KEY: modified_base
<222> LOCATION: (15)..(16)
<223> OTHER INFORMATION: phosphorothioate linkage
<220> FEATURE:
<221> NAME/KEY: modified_base
<222> LOCATION: (16)..(17)
<223> OTHER INFORMATION: phosphorothioate linkage
<220> FEATURE:
<221> NAME/KEY: modified_base
<222> LOCATION: (17)..(18)
<223> OTHER INFORMATION: phosphorothioate linkage
<220> FEATURE:
<221> NAME/KEY: modified_base
<222> LOCATION: (18)..(19)
<223> OTHER INFORMATION: phosphorothioate linkage
<220> FEATURE:
<221> NAME/KEY: modified_base
<222> LOCATION: (19)..(20)
<223> OTHER INFORMATION: phosphorothioate linkage

<400> SEQUENCE: 8
gtcggtgaac aggttagaga                                              20

<210> SEQ ID NO 9
<211> LENGTH: 16
<212> TYPE: DNA
<213> ORGANISM: Artificial Sequence
<220> FEATURE:
<223> OTHER INFORMATION: Labelled primer

<400> SEQUENCE: 9
cctaacggct aatcgc                                                  16

<210> SEQ ID NO 10
<211> LENGTH: 16
<212> TYPE: DNA
<213> ORGANISM: Artificial Sequence
<220> FEATURE:
<223> OTHER INFORMATION: Labelled primer
<220> FEATURE:

```
<221> NAME/KEY: modified_base
<222> LOCATION: (1)..(2)
<223> OTHER INFORMATION: phosphorothioate linkage
<220> FEATURE:
<221> NAME/KEY: modified_base
<222> LOCATION: (3)..(4)
<223> OTHER INFORMATION: phosphorothioate linkage
<220> FEATURE:
<221> NAME/KEY: modified_base
<222> LOCATION: (4)..(5)
<223> OTHER INFORMATION: phosphorothioate linkage
<220> FEATURE:
<221> NAME/KEY: modified_base
<222> LOCATION: (5)..(6)
<223> OTHER INFORMATION: phosphorothioate linkage
<220> FEATURE:
<221> NAME/KEY: modified_base
<222> LOCATION: (6)..(7)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (8)..(9)
<223> OTHER INFORMATION: phosphorothioate linkage
<220> FEATURE:
<221> NAME/KEY: modified_base
<222> LOCATION: (10)..(11)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (12)..(13)
<223> OTHER INFORMATION: phosphorothioate linkage
<220> FEATURE:
<221> NAME/KEY: modified_base
<222> LOCATION: (13)..(14)
<223> OTHER INFORMATION: phosphorothioate linkage
<220> FEATURE:
<221> NAME/KEY: modified_base
<222> LOCATION: (14)..(15)
<223> OTHER INFORMATION: phosphorothioate linkage
<220> FEATURE:
<221> NAME/KEY: modified_base
<222> LOCATION: (15)..(16)
<223> OTHER INFORMATION: phosphorothioate linkage

<400> SEQUENCE: 10
cctaacggct aatcgc                                                 16

<210> SEQ ID NO 11
<211> LENGTH: 16
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (2)..(3)
<223> OTHER INFORMATION: phosphorothioate linkage
<220> FEATURE:
<221> NAME/KEY: modified_base
<222> LOCATION: (4)..(5)
<223> OTHER INFORMATION: phosphorothioate linkage
<220> FEATURE:
<221> NAME/KEY: modified_base
<222> LOCATION: (6)..(7)
<223> OTHER INFORMATION: phosphorothioate linkage
<220> FEATURE:
<221> NAME/KEY: modified_base
<222> LOCATION: (8)..(9)
<223> OTHER INFORMATION: phosphorothioate linkage
```

-continued

<220> FEATURE:
<221> NAME/KEY: modified_base
<222> LOCATION: (10)..(11)
<223> OTHER INFORMATION: phosphorothioate linkage
<220> FEATURE:
<221> NAME/KEY: modified_base
<222> LOCATION: (12)..(13)
<223> OTHER INFORMATION: phosphorothioate linkage
<220> FEATURE:
<221> NAME/KEY: modified_base
<222> LOCATION: (14)..(15)
<223> OTHER INFORMATION: phosphorothioate linkage

<400> SEQUENCE: 11
cctaacggct aatcgc                                                      16

<210> SEQ ID NO 12
<211> LENGTH: 16
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (1)..(2)
<223> OTHER INFORMATION: phosphorothioate linkage
<220> FEATURE:
<221> NAME/KEY: modified_base
<222> LOCATION: (2)..(3)
<223> OTHER INFORMATION: phosphorothioate linkage
<220> FEATURE:
<221> NAME/KEY: modified_base
<222> LOCATION: (3)..(4)
<223> OTHER INFORMATION: phosphorothioate linkage
<220> FEATURE:
<221> NAME/KEY: modified_base
<222> LOCATION: (4)..(5)
<223> OTHER INFORMATION: phosphorothioate linkage
<220> FEATURE:
<221> NAME/KEY: modified_base
<222> LOCATION: (5)..(6)
<223> OTHER INFORMATION: phosphorothioate linkage
<220> FEATURE:
<221> NAME/KEY: modified_base
<222> LOCATION: (6)..(7)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (8)..(9)
<223> OTHER INFORMATION: phosphorothioate linkage
<220> FEATURE:
<221> NAME/KEY: modified_base
<222> LOCATION: (9)..(10)
<223> OTHER INFORMATION: phosphorothioate linkage
<220> FEATURE:
<221> NAME/KEY: modified_base
<222> LOCATION: (10)..(11)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (12)..(13)
<223> OTHER INFORMATION: phosphorothioate linkage
<220> FEATURE:
<221> NAME/KEY: modified_base
<222> LOCATION: (13)..(14)
<223> OTHER INFORMATION: phosphorothioate linkage
<220> FEATURE:
<221> NAME/KEY: modified_base
<222> LOCATION: (14)..(15)

```
<223> OTHER INFORMATION: phosphorothioate linkage
<220> FEATURE:
<221> NAME/KEY: modified_base
<222> LOCATION: (15)..(16)
<223> OTHER INFORMATION: phosphorothioate linkage

<400> SEQUENCE: 12
cctaacggct aatcgc                                                     16

<210> SEQ ID NO 13
<211> LENGTH: 15
<212> TYPE: DNA
<213> ORGANISM: Artificial Sequence
<220> FEATURE:
<223> OTHER INFORMATION: Labelled primer

<400> SEQUENCE: 13
aacctgttca ccgac                                                      15

<210> SEQ ID NO 14
<211> LENGTH: 15
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (2)..(3)
<223> OTHER INFORMATION: phosphorothioate linkage
<220> FEATURE:
<221> NAME/KEY: modified_base
<222> LOCATION: (4)..(5)
<223> OTHER INFORMATION: phosphorothioate linkage
<220> FEATURE:
<221> NAME/KEY: modified_base
<222> LOCATION: (6)..(7)
<223> OTHER INFORMATION: phosphorothioate linkage
<220> FEATURE:
<221> NAME/KEY: modified_base
<222> LOCATION: (8)..(9)
<223> OTHER INFORMATION: phosphorothioate linkage
<220> FEATURE:
<221> NAME/KEY: modified_base
<222> LOCATION: (10)..(11)
<223> OTHER INFORMATION: phosphorothioate linkage
<220> FEATURE:
<221> NAME/KEY: modified_base
<222> LOCATION: (12)..(13)
<223> OTHER INFORMATION: phosphorothioate linkage
<220> FEATURE:
<221> NAME/KEY: modified_base
<222> LOCATION: (14)..(15)
<223> OTHER INFORMATION: phosphorothioate linkage

<400> SEQUENCE: 14
aacctgttca ccgac                                                      15

<210> SEQ ID NO 15
<211> LENGTH: 15
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (1)..(2)
<223> OTHER INFORMATION: phosphorothioate linkage
<220> FEATURE:
<221> NAME/KEY: modified_base
<222> LOCATION: (3)..(4)
<223> OTHER INFORMATION: phosphorothioate linkage
<220> FEATURE:
<221> NAME/KEY: modified_base
```

```
<222> LOCATION: (5)..(6)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (9)..(10)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (13)..(14)
<223> OTHER INFORMATION: phosphorothioate linkage

<400> SEQUENCE: 15
aacctgttca ccgac                                                    15

<210> SEQ ID NO 16
<211> LENGTH: 15
<212> TYPE: DNA
<213> ORGANISM: Artificial Sequence
<220> FEATURE:
<223> OTHER INFORMATION: Labelled primer
<220> FEATURE:
<221> NAME/KEY: modified_base
<222> LOCATION: (1)..(2)
<223> OTHER INFORMATION: phosphorothioate linkage
<220> FEATURE:
<221> NAME/KEY: modified_base
<222> LOCATION: (2)..(3)
<223> OTHER INFORMATION: phosphorothioate linkage
<220> FEATURE:
<221> NAME/KEY: modified_base
<222> LOCATION: (3)..(4)
<223> OTHER INFORMATION: phosphorothioate linkage
<220> FEATURE:
<221> NAME/KEY: modified_base
<222> LOCATION: (4)..(5)
<223> OTHER INFORMATION: phosphorothioate linkage
<220> FEATURE:
<221> NAME/KEY: modified_base
<222> LOCATION: (5)..(6)
<223> OTHER INFORMATION: phosphorothioate linkage
<220> FEATURE:
<221> NAME/KEY: modified_base
<222> LOCATION: (6)..(7)
<223> OTHER INFORMATION: phosphorothioate linkage
<220> FEATURE:
<221> NAME/KEY: modified_base
<222> LOCATION: (7)..(8)
<223> OTHER INFORMATION: phosphorothioate linkage
<220> FEATURE:
<221> NAME/KEY: modified_base
<222> LOCATION: (8)..(9)
<223> OTHER INFORMATION: phosphorothioate linkage
<220> FEATURE:
<221> NAME/KEY: modified_base
<222> LOCATION: (9)..(10)
<223> OTHER INFORMATION: phosphorothioate linkage
<220> FEATURE:
<221> NAME/KEY: modified_base
<222> LOCATION: (10)..(11)
<223> OTHER INFORMATION: phosphorothioate linkage
<220> FEATURE:
<221> NAME/KEY: modified_base
<222> LOCATION: (11)..(12)
<223> OTHER INFORMATION: phosphorothioate linkage
<220> FEATURE:
<221> NAME/KEY: modified_base
<222> LOCATION: (12)..(13)
<223> OTHER INFORMATION: phosphorothioate linkage
<220> FEATURE:
```

```
<221> NAME/KEY: modified_base
<222> LOCATION: (13)..(14)
<223> OTHER INFORMATION: phosphorothioate linkage
<220> FEATURE:
<221> NAME/KEY: modified_base
<222> LOCATION: (14)..(15)
<223> OTHER INFORMATION: phosphorothioate linkage

<400> SEQUENCE: 16
aacctgttca ccgac                                                      15

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
gcgattagcc gttaggatga ctgagtgcag gttcagacgt cc                         42

<210> SEQ ID NO 18
<211> LENGTH: 42
<212> TYPE: DNA
<213> ORGANISM: Artificial Sequence
<220> FEATURE:
<223> OTHER INFORMATION: primer

<400> SEQUENCE: 18
gtcggtgaac aggttagaga ctgagtgcag gttcagacgt ct                         42

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
ctcccttcca cctccgtacc at                                               22
```

POLYMERASE CHAIN REACTION DETECTION SYSTEM

CROSS REFERENCE TO RELATED APPLICATION

This application is a divisional application of, and claims the benefit under 35 U.S.C. §§120 and 121 of, U.S. patent application Ser. No. 13/427,686, filed Mar. 22, 2012, the contents of which are expressly incorporated by reference herein in their entirety.

SEQUENCE LISTING

This application contains a Sequence Listing, which has been submitted in ASCII format via EFS-Web and is hereby incorporated by reference in its entirety. Said Sequence Listing was filed in the parent application, U.S. patent application Ser. No. 13/427,686, filed Mar. 22, 2012, on two (2) identical compact discs filed in compliance with 1.52(e), created in July 2012, including nucleic acid SEQ ID NOS. 1-19. The compact discs each contain a single 13,881 byte file named "WOP6799 Sequence Listing_ST25.txt" created on Jun. 4, 2012.

INTRODUCTION

The present invention relates to methods and kits for nucleic acid detection in an assay system.

BACKGROUND OF THE INVENTION

The polymerase chain reaction (PCR) is a powerful method for the rapid and exponential amplification of target nucleic acid sequences. PCR has facilitated the development of gene characterization and molecular cloning technologies including the direct sequencing of PCR amplified DNA, the determination of allelic variation, and the detection of infectious and genetic disease disorders. PCR is performed by repeated cycles of heat denaturation of a DNA template containing the target sequence, annealing of opposing primers to the complementary DNA strands, and extension of the annealed primers with a DNA polymerase. Multiple PCR cycles result in the exponential amplification of the nucleotide sequence delineated by the flanking amplification primers. The incorporation of a thermostable DNA polymerase into the PCR protocol obviates the need for repeated enzyme additions and permits elevated annealing and primer extension temperatures which enhance the specificity of primer: template associations. Taq DNA polymerase thus serves to increase the specificity and simplicity of PCR.

In many PCR based reactions, a signal producing system is employed, e.g. to detect the production of amplified product. One type of signal producing system that is used in PCR based reactions is the fluorescence energy transfer (FRET) system, in which a nucleic acid detector includes fluorescence donor and acceptor groups. FRET label systems include a number of advantages over other labelling systems, including the ability to perform homogeneous assays in which a separation step of bound vs. unbound labelled nucleic acid detector is not required. A primary problem with many prior art techniques is linked to the synthesis of dual labelled fluorescent oligonucleotides. European Patent Application EP1726664 discloses a detection system which overcomes this problem by using single-labelled oligonucleotide sequences of differing melting temperature (Tm) that hybridise to one another in free solution to form a fluorescent quenched pair, that upon introduction of a complementary sequence to one or both sequences generates a measurable signal, one of the sequences being of a Tm that is below the annealing temperature (Ta) of the PCR process.

In detection systems using a labelled nucleic acid detector, high fidelity amplification is critical. Due to the nature of the PCR process and Taq DNA polymerase such methods can suffer from alternative side-reactions to the desired polymerisation reaction. For example, PCR can suffer from non-specific amplification when the reaction is assembled at ambient temperature. At sub-PCR temperatures, Taq polymerase retains a fraction of its activity and can therefore extend primers that are not complementarily annealed, leading to the formation of undesired products. The newly-synthesized region then acts as a template for further primer extension and synthesis of undesired amplification products. However, if the reaction is heated to temperatures of around 50° C. or above before polymerization begins, the stringency of primer annealing is increased, and synthesis of undesired PCR products is avoided or reduced.

Primer-dimer is also a common side-reaction affecting PCR. Accumulation of primer-dimer occurs because of the hybridisation and extension of the primers to each other. Formation of primer-dimer results in the depletion of the reagents and hence overall reduction of PCR efficiency.

Hot-start PCR is a method to reduce non-specific amplification and hence limit the formation of primer-dimers and many different approaches have been developed to achieve this see, for example, Moretti, T. et al. Enhancement of PCR amplification yield and specificity using AmpliTaq Gold DNA polymerase. *BioTechniques* 25, 716-22 (1998) and Hot Start PCR with heat-activatable primers: a novel approach for improved PCR performance *Nucleic Acids Res* (2008) 36(20): e131. However, such techniques only achieve partial alleviation of such problems. As any error in sequences, non-polymerisation based reactions or primer mispriming such as primer dimerisation may cause the production of weak signal or the wrong signal being produced, particularly in allele specific PCR, further improvement of these weak or incorrect signals would be desirable.

Phosphorothioates (or S-oligos) are a variant of normal DNA in which one of the nonbridging oxygens is replaced by sulfur. Examples of phosphodiester and phosphorothioate internucleotide linkages are shown below:

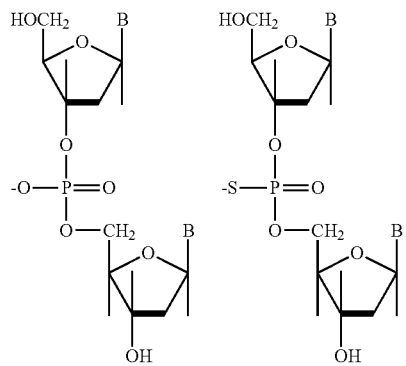

The phosphorothioate bond substitutes a sulphur atom for a non-bridging oxygen in the phosphate backbone of an oligonucleotide, rendering the internucleotide linkage resistant to nuclease degradation. Phosphorothioates can be introduced at either the 5'- or 3'-end of the oligo to inhibit exonuclease degradation. In antisense oligonucleotides, phosphorothioates are also introduced internally to limit attack by endonucleases. The synthesis of phosphorothioate containing oligonucleotides is described, for example in Verma S. and Eckstein, F. (1998). MODIFIED OLIGO-NUCLEOTIDES: Synthesis and Strategy for Users. Annu. Rev. Biochem. 1998. 67:99-134 and Curr Protoc Nucleic Acid Chem. 2009 March; Chapter 4: Unit 4.34. DNA oligonucleotides containing stereodefined phosphorothioate linkages in selected positions. Nawrot B, Rebowska B.

As mentioned above the sulfurisation of the internucleotide bond reduces the action of endo- and exonucleases2 including 5'→3' and 3'→5' DNA POL 1 exonuclease, nucleases S1 and P1, RNases, serum nucleases and snake venom phosphodiesterase. The nuclease resistant attribute of the S-oligo in conjunction with high fidelity PCR employing the use of exo+DNA polymerases has been demonstrated see, for example, Nucl. Acids Res. (2003) 31 (3): e7. doi: 10.1093/nar/gng007. Taq DNA polymerase possesses no 3'→5' Exonuclease (Kenneth R. Tindall, Thomas A. Kunkel, Biochemistry, 1988, 27 (16), p 6008-6013). Enhanced discrimination of single nucleotide polymorphisms by phosphorothioate modification in the presence of a proof-reading polymerase has also been reported. Phosphorothioation increases specificity, reducing incidences of primer-dimer interactions, however it is reported that 3' nuclease functionality is required for the improvement to PCR and it has been demonstrated that in conjunction with Allele Specific PCR the use of S-oligos offer no benefit when used in conjunction with Taq DNA polymerase see, for example, Zhang, J. and Li, K. (2003) Single-Base Discrimination Mediated by Proofreading 3' Phosphorothioate-Modified Primers. Molecular Biotechnology 25, 223-227.

There is a need for easy-to-synthesise, low cost and reliable specific detection systems for use in the detection of primer extension products, e.g. in homogeneous PCR assays, which address the problems encountered with existing detection systems for PCR. Contrary to conventional scientific knowledge the present invention is based on the finding that S-oligos can be used successfully, and result in improvements, in nucleic acid detection assay systems.

SUMMARY OF THE INVENTION

According to the invention there is provided a method for reducing non-specific amplification and/or formation of primer-dimers in a template dependent primer extension reaction comprising conducting a primer extension reaction in the presence of a polymerase lacking 3'→5' nuclease activity, wherein one or more of the primers contains at least one phosphorothioate group.

Kits and compositions for use in such methods are also provided.

DETAILED DESCRIPTION OF THE INVENTION

Figure 1A:
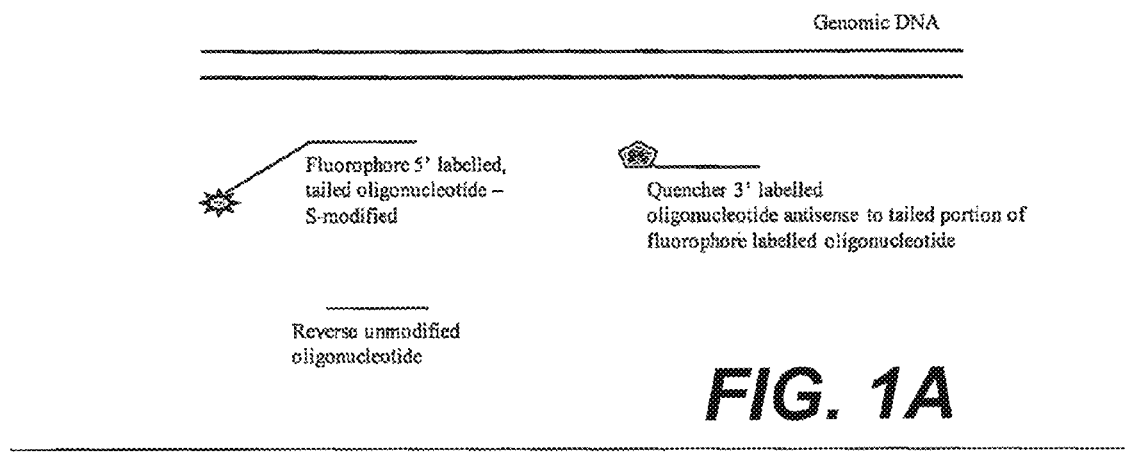
FIG. 1 A-E shows a simple reaction schema for direct detection of a DNA sequence embodying the method of the present invention.
Figure 1B:
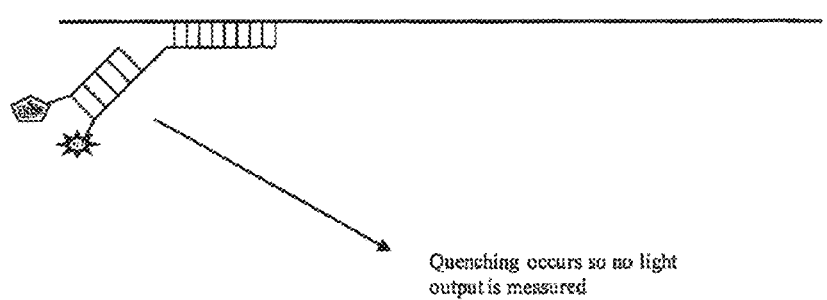
Figure 1C:
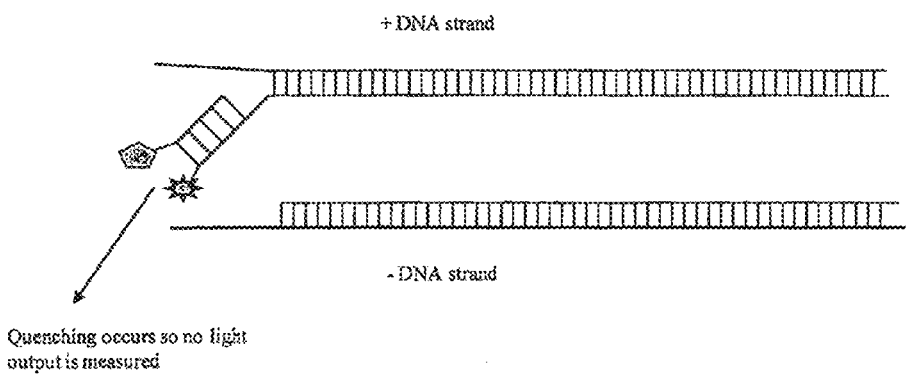
Figure 1D:
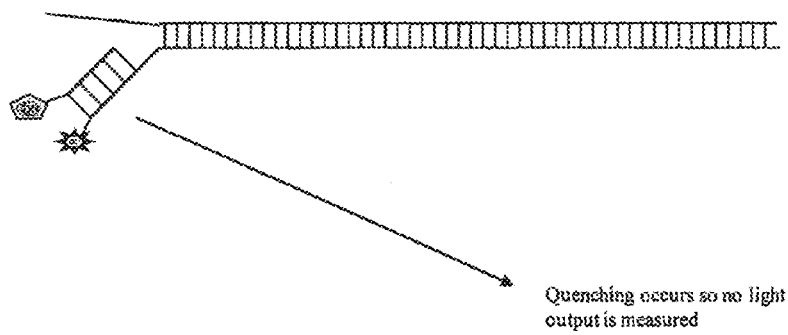
Figure 1E:
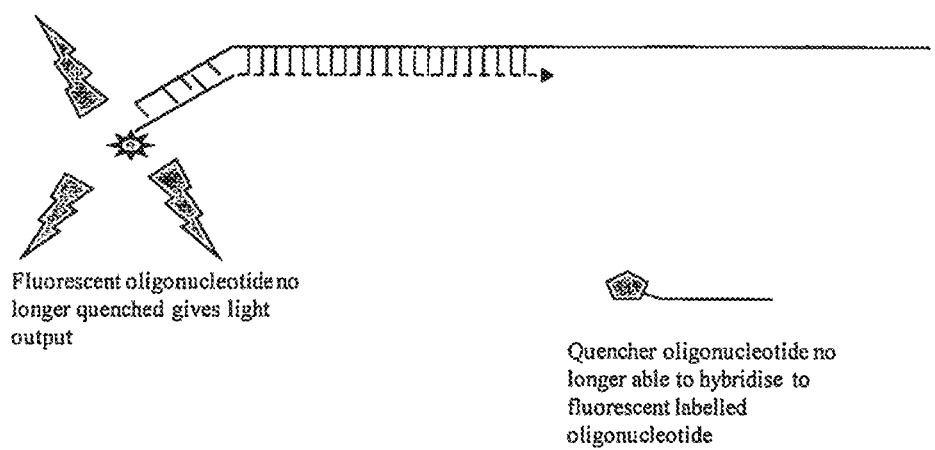
Figure 2A:
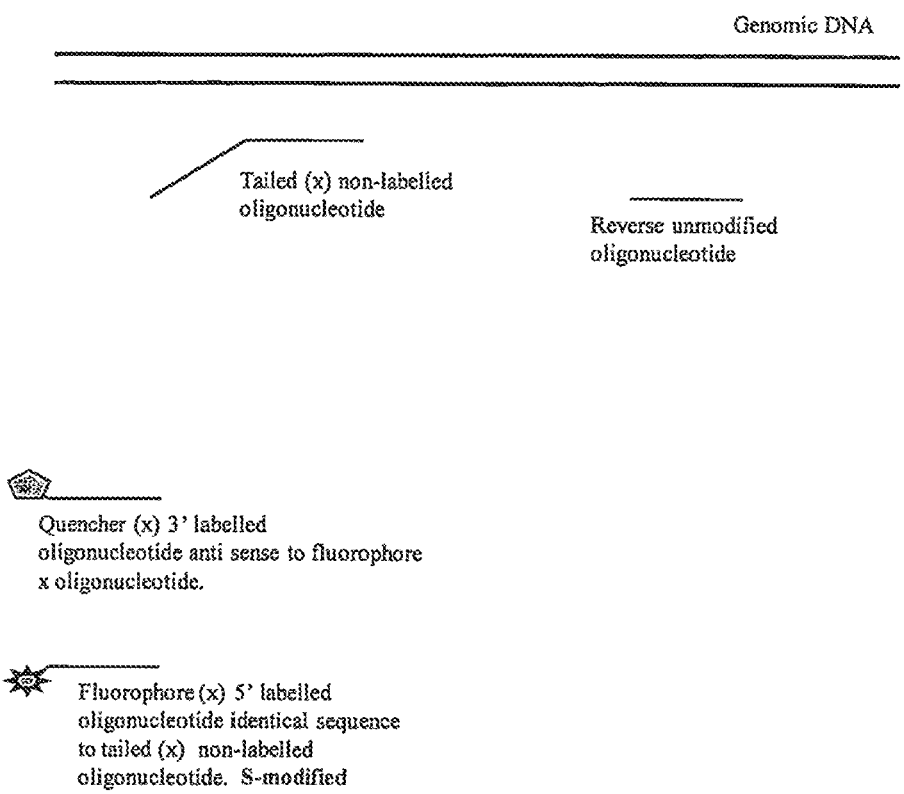
FIG. 2 A-E shows a simple reaction schema for indirect (real-time) detection of a DNA sequence embodying the method of the present invention.
Figure 2B:
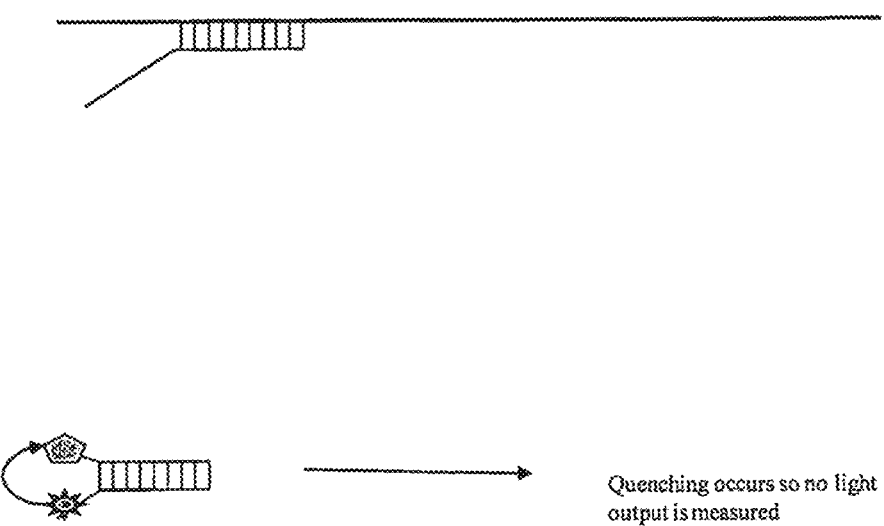
Figure 2C:
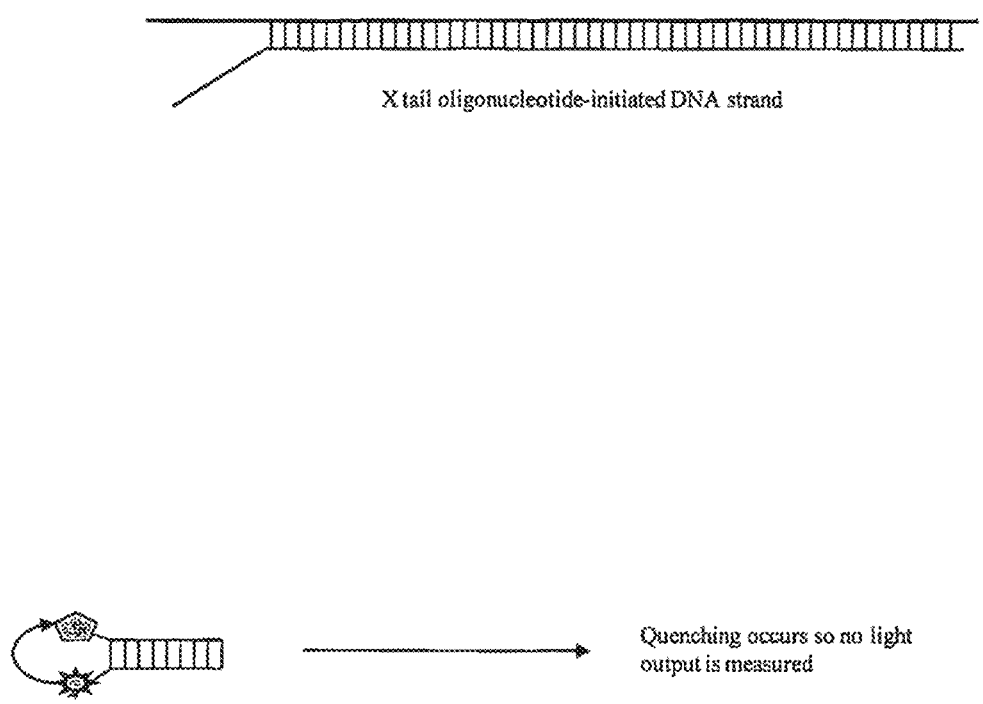
Figure 2D:
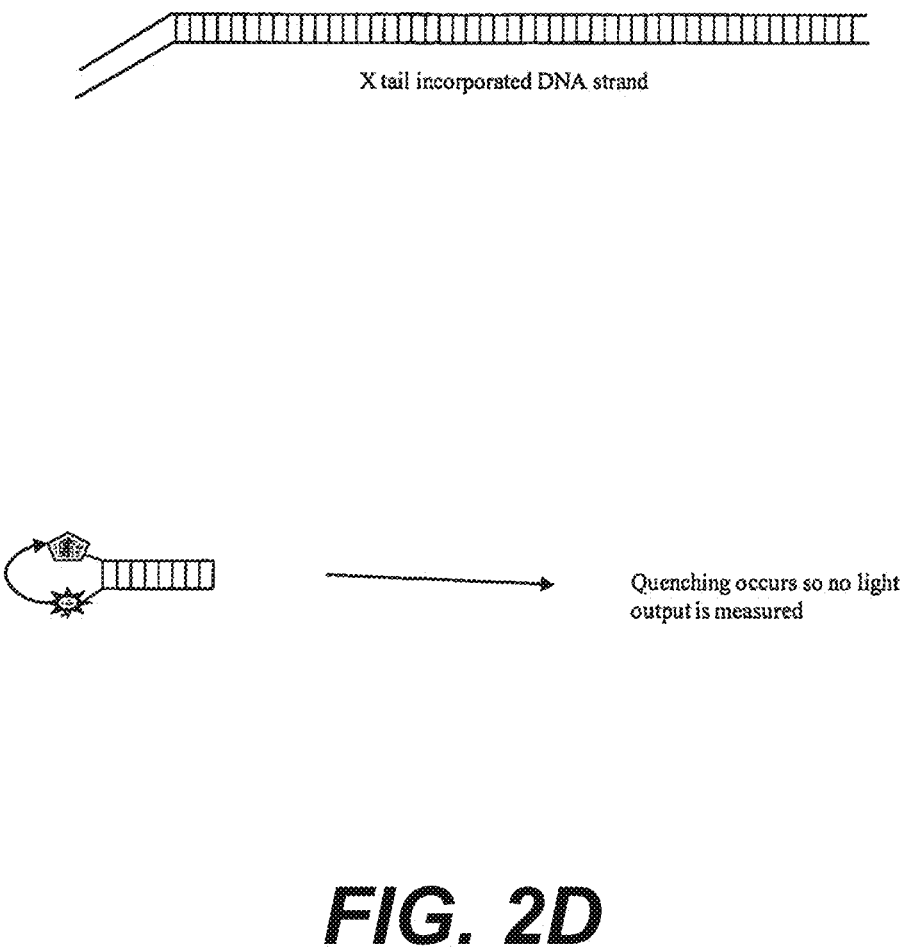
Figure 2E:
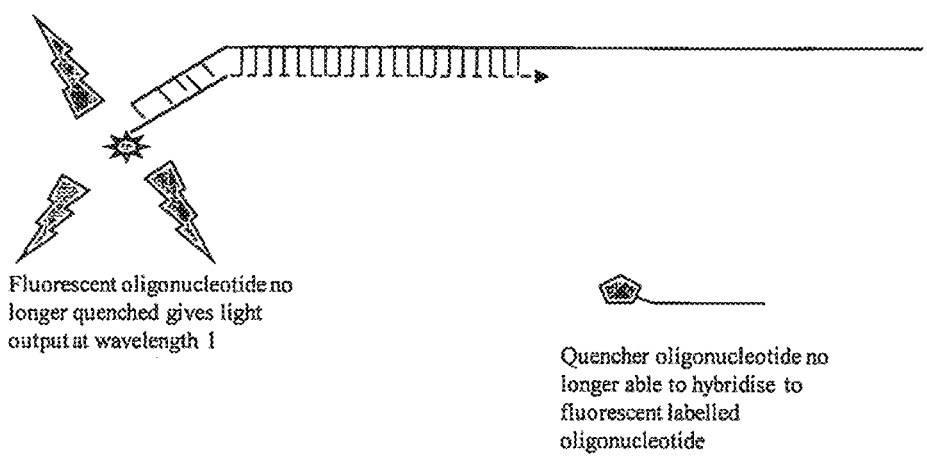
Figure 3A:
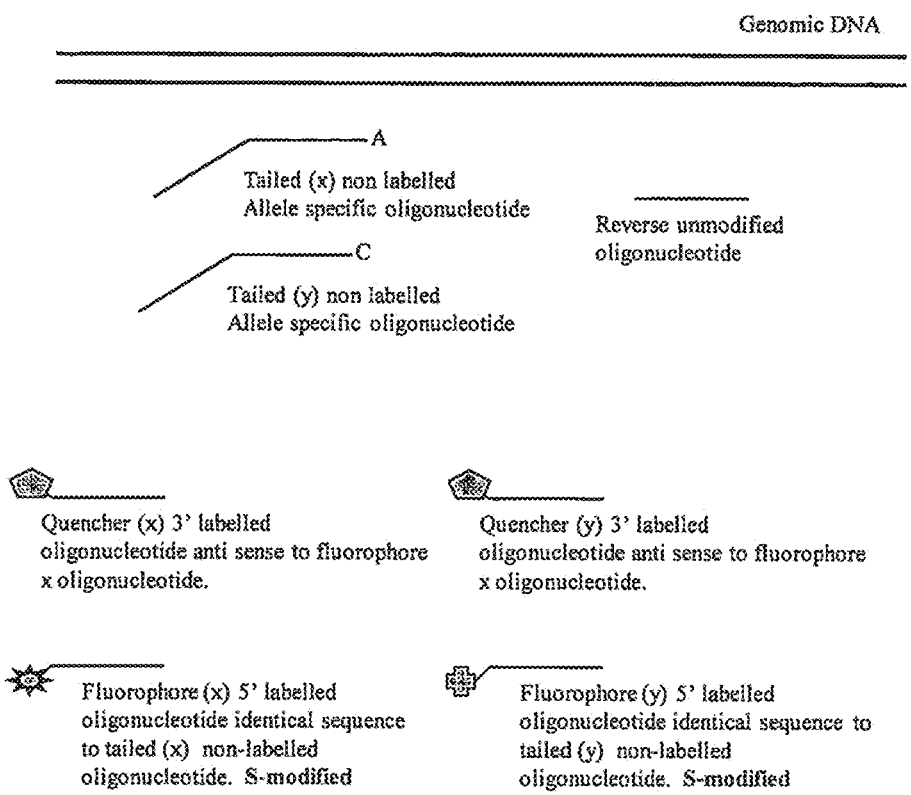
FIG. 3 A-E shows a simple reaction schema for indirect (end-point) detection of a DNA sequence in SNP Genotyping embodying the method of the present invention.
Figure 3B:
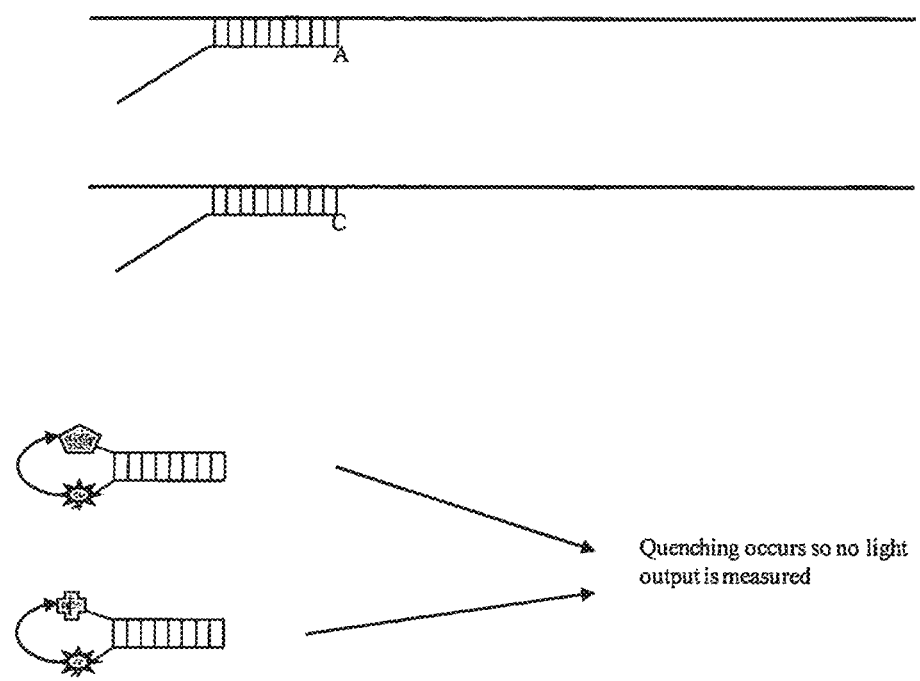
Figure 3C:
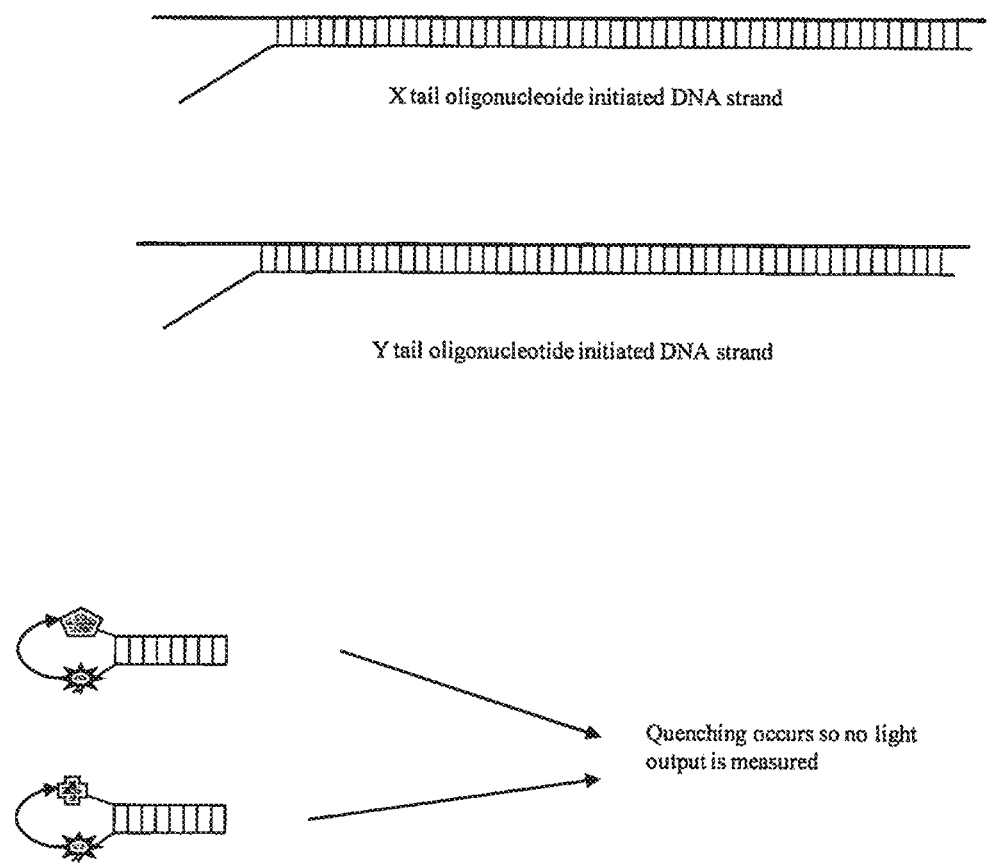
Figure 3D:
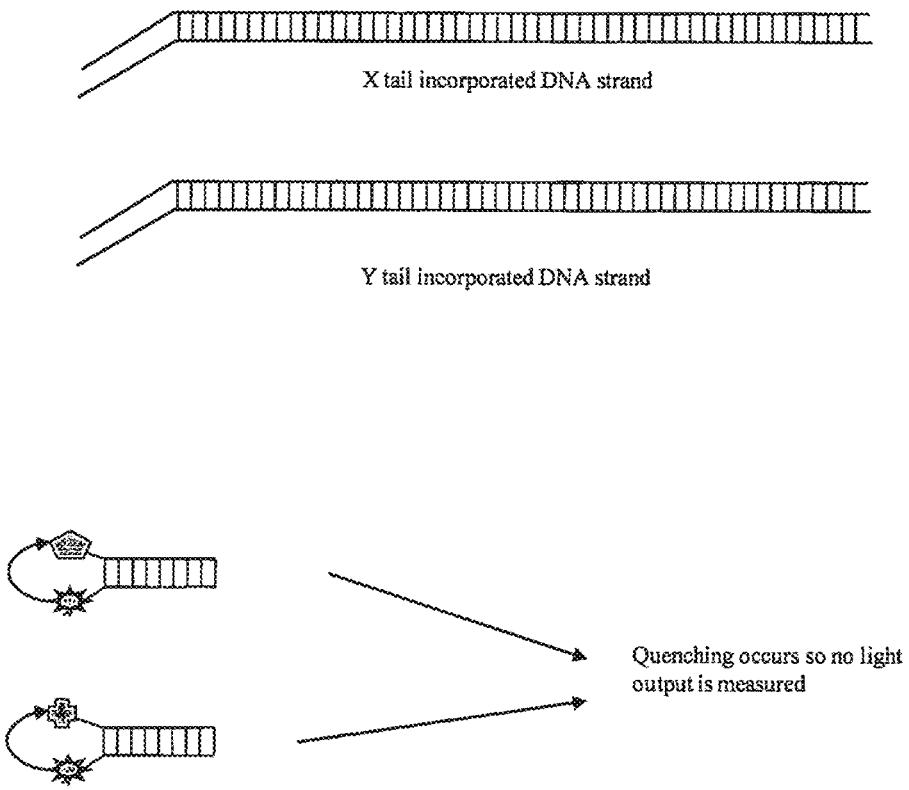
Figure 3E:
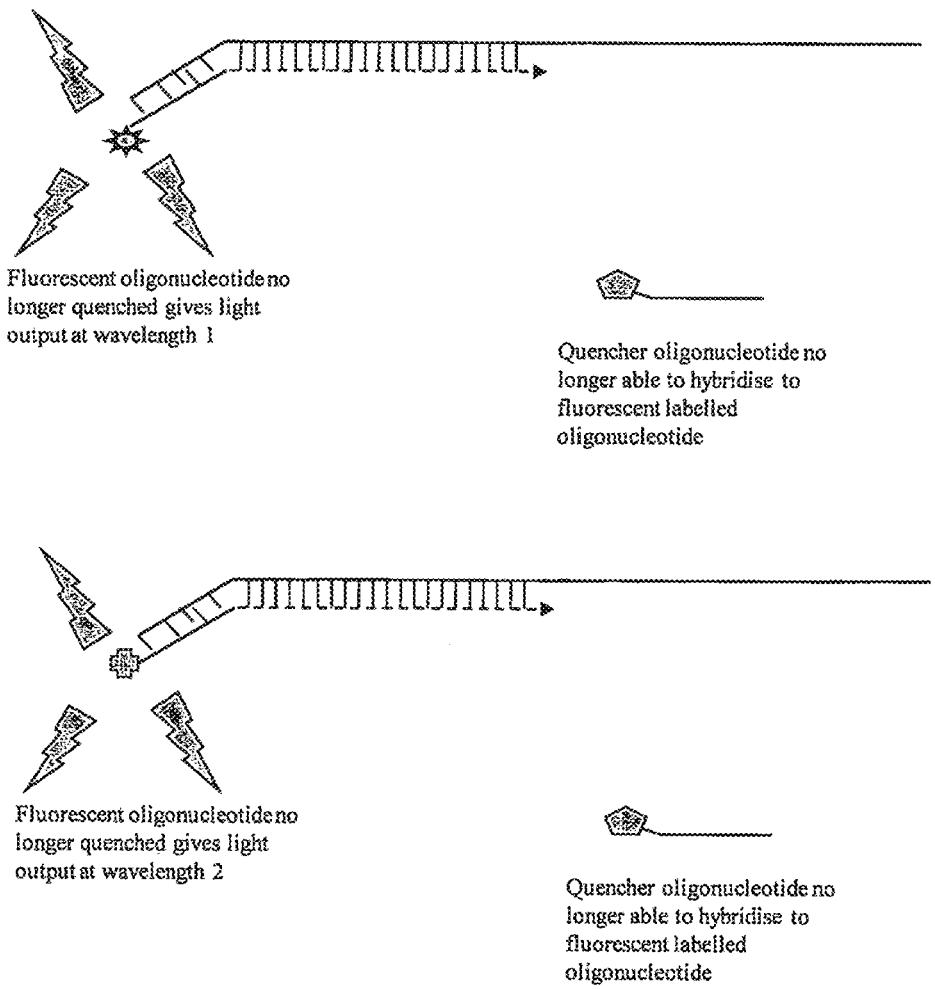

According to the invention there is provided a method for reducing non-specific amplification and/or formation of primer-dimers in a template dependent primer extension reaction comprising conducting a primer extension reaction in the presence of a polymerase lacking 3'→5' nuclease activity, wherein one or more of the primers contains at least one phosphorothioate group.

The method of the invention preferably comprises the use of at least two single-labelled oligonucleotide sequences that hybridise to one another in free solution to form a fluorescent quenched pair, that upon introduction of a complementary sequence to one or both sequences generates a measurable signal, wherein one or more of the primers is modified with at least one phosphorothioate group.

In one embodiment of the invention the two single-labelled oligonucleotide sequences are of differing Tm. When the oligonucleotide sequences are of differing Tm then one of the sequences may have a Tm that is at or below the Ta of the primer extension reaction e.g. PCR process. The other may have a Tm that is suitably not below the Ta but preferably above it and more preferably substantially above it. In one embodiment the quencher oligonucleotide has a Tm above the Ta.

A commonly used formula for determining the Tm of a sequence is Tm=4(G+C)+2(A+T), and thus the low Tm of one sequence may, in principle, be attained by a shorter length and/or a reduced (G+C)/(A+T) ratio relative to the other sequence of the reporter pair.

In some aspects of the invention it is preferred that one of the single-labelled oligonucleotide sequences be more than 10 bases longer than the other and preferably at least 15 bases longer.

The invention also provides a method for the detection of a primer extension product produced in the presence of a polymerase lacking 3'→5' exonuclease activity, the method comprising the steps of:

a) providing at least two single-labelled oligonucleotide sequences, e.g. of differing Tm, that hybridise to one another in free solution to form a fluorescent quenched pair, that upon introduction of a complementary sequence to one or both sequences generates a measurable signal, wherein at least one of the oligonucleotide sequences contains at least one phosphorothioate group;

b) providing at least one primer and initiating the primer extension reaction thereby generating a complementary sequence to at least one of the single-labelled oligonucleotide sequences; and c) measuring the detectable signal that is generated.

In a further preferred aspect of the invention the method comprises a method for the detection of a primer extension product produced in the presence of a polymerase lacking 3'→5' exonuclease activity using PCR, the method comprising the steps of:

a) providing a first single-labelled oligonucleotide sequence and at least a second single-labelled oligonucleotide sequence, e.g. where the first and second oligonucleotide sequences are of differing Tm, in which the first and second oligonucleotide sequences hybridise to one another in free solution to form a fluorescent quenched pair and at least one primer, and e.g. where one of the first and second oligonucleotide sequences is of a Tm that is at or below the Ta of the PCR process, wherein at least one of the oligonucleotide sequences contain at least one phosphorothioate group, the at least one primer comprising at least one unlabelled tailed primer, the unlabelled tailed primer having a tail region, the tail region comprising an oligonucleotide sequence complementary to an oligonucleotide sequence of the second single-labelled oligonucleotide sequence, the first single-labelled oligonucleotide sequence being a primer from which DNA synthesis is initiated once a complementary sequence to the first single-labelled oligonucleotide sequence has been generated during the PCR process, such that the second single-labelled oligonucleotide sequence is no longer able to hybridise to the first single-labelled oligonucleotide sequence, whereby a measurable signal is generated;
b) initiating the primer extension reaction thereby generating a complementary sequence to at least one of the single-labelled oligonucleotide sequences; and
c) measuring the detectable signal that is generated.

In a further preferred aspect of the invention the method comprises a method for the detection of a primer extension product produced in the presence of a polymerase lacking 3'→5' exonuclease activity using PCR, the method comprising the steps of:
a) providing a first single-labelled oligonucleotide sequence and at least a second single-labelled oligonucleotide sequence, e.g. where the first and second oligonucleotide sequences are of differing Tm, in which the first and second oligonucleotide sequences hybridise to one another in free solution to form a fluorescent quenched pair and at least one primer, and e.g. where one of the first and second oligonucleotide sequences is of a Tm that is at or below the Ta of the PCR process, wherein at least one of the oligonucleotide sequences contain at least one phosphorothioate group, the at least one primer comprising at least one unlabelled tailed primer, the unlabelled tailed primer having a tail region, the tail region comprising an oligonucleotide sequence identical or substantially homologous to an oligonucleotide sequence of the first single-labelled oligonucleotide sequence, the first single-labelled oligonucleotide sequence being a primer from which DNA synthesis is initiated once a complementary sequence to the first single-labelled oligonucleotide sequence has been generated during the PCR process, such that the second single-labelled oligonucleotide sequence is no longer able to hybridise to the first single-labelled oligonucleotide sequence, whereby a measurable signal is generated;
b) initiating the primer extension reaction thereby generating a complementary sequence to at least one of the single-labelled oligonucleotide sequences; and
c) measuring the detectable signal that is generated.

The invention also provides a kit for the detection of a primer extension product produced in the presence of a polymerase lacking 3'→5' exonuclease activity, that comprises at least two single-labelled oligonucleotide sequences e.g. of differing Tm, that hybridise to one another in free solution to form a fluorescent quenched pair, that upon introduction of a complementary sequence to one or both sequences generates a measurable signal, wherein at least one of the oligonucleotide sequences contain at least one phosphorothioate group.

The kits according to the invention may also contain a polymerase lacking 3'→5' exonuclease activity and/or other components suitable for use in primer extension reactions such as magnesium salts, dNTPs etc.

In the present invention, all or at least one of primers used in the methods may contain phosphorothioate-modified bases. The number of phosphodiester linkages replaced by phosphorothioates in any given primer can range from one to all of the phosphodiester bonds being replaced by phosphothioates. The primer(s) may contain phosphorothioates at the 5' and/or 3' terminii, however it is preferred that, as an alternative to or addition to such terminal modifications, at least one of the internal bases of the primer is a phosphorothioate. For example 10-90%, 20-80%, 30-70% or 40-60% of the bases may be phosphorothioates. In one embodiment the phosphorothioate-modified bases are separated by at least one, e.g. one to three, unmodified (phosphorodiester) bases. In a preferred embodiment alternate bases within the primer(s) are phosphorothioates.

Use of phosphorothioate modification on alternate bases of fluorophore-labelled primers (referred to herein as semi-S modification) in conjunction with unmodified quenchers represents a preferred embodiment of the invention as these give particularly enhanced discrimination and signal intensity of the PCR.

Examples of differing phosphorothioate-modifications which may be used in the invention are illustrated below in primers labelled with fluorophores or quenchers, where * denotes a phosphorothioate:

```
Unmodified FAM Fluor:
                                        (SEQ ID NO: 1)
5'-FAM-GCGATTAGCCGTTAGGATGA 3'

3' S FAM Fluor:
                                        (SEQ ID NO: 2)
5'-FAM-GCGATTAGCCGTTAGGATG*A 3'

Semi S FAM Fluor:
                                        (SEQ ID NO: 3)
5'-FAM-G*CG*AT*TA*GC*CG*TT*AG*GA*TG*A 3'

Full S FAM Fluor:
                                        (SEQ ID NO: 4)
5'-FAM-G*C*G*A*T*T*A*G*C*C*G*T*T*AG*G*

A*T*G*A 3'

Unmodified HEX Fluor:
                                        (SEQ ID NO: 5)
5'-HEX-GTCGGTGAACAGGTTAGAGA 3'

3' S HEX Fluor:
                                        (SEQ ID NO: 6)
5'-HEX-GTCGGTGAACAGGTTAGAG*A 3'

Semi S HEX Fluor:
                                        (SEQ ID NO: 7)
5'-HEX-G*TC*GG*TG*AA*CA*GG*TT*AG*AG*A 3'

Full S HEX Fluor:
                                        (SEQ ID NO: 8)
5'-HEX-G*T*C*G*G*T*G*A*A*C*A*G*G*T*T*

A*G*A*G*A 3'

Standard FAM Quencher:
                                        (SEQ ID NO: 9)
5' CCTAACGGCTAATCGC-3' Dabsyl Semi S FAM Quencher V1.0:
                                        (SEQ ID NO: 10)
5' C*CT*AA*CG*GC*TA*AT*CG*C-3' Dabsyl Semi S FAM Quencher V2.0:
                                        (SEQ ID NO: 11)
5' CC*TA*AC*GG*CT*AA*TC*GC-3' Dabsyl
```

```
-continued
Full S FAM Quencher:
                                    (SEQ ID NO: 12)
5' C*C*T*A*A*C*G*G*C*T*A*A*T*C*G*C-3' Dabsyl Standard HEX Quencher:
                                    (SEQ ID NO: 13)
5' AACCTGTTCACCGAC-3' Dabsyl Semi S HEX Quencher V1.0:
                                    (SEQ ID NO: 14)
5' AA*CC*TG*TT*CA*CC*GA*C-3' Dabsyl Semi S HEX Quencher V2.0:
                                    (SEQ ID NO: 15)
5' A*AC*CT*GT*TC*AC*CG*AC-3' Dabsyl Full S HEX Quencher:
                                    (SEQ ID NO: 16)
5' A*A*C*C*T*G*T*T*C*A*C*C*G*A*C-3' Dabsyl
```

Oligonucleotide sequences containing at least one phosphorothioate group for use in the present invention may be synthesised by methods known to those skilled in the art.

The present invention finds use in a variety of different applications, and is particularly suited for use in PCR based reactions, including SNP detection applications, allelic variation detection applications, real-time PCR and the like.

As indicated above, the present invention provides methods reducing non-specific amplification and/or formation of primer-dimers in a template dependent primer extension reaction and for detecting the production of primer extension products in a primer extension reaction mixture, e.g. determining whether primer extension products are produced in a primer extension reaction. By primer extension product is meant a nucleic acid molecule that results from a template dependent primer extension reaction. Template dependent primer extension reactions are those reactions in which a polymerase extends a nucleic acid primer molecule that is hybridized to a template nucleic acid molecule, where the sequence of bases that is added to the terminus of the primer nucleic acid molecule is determined by the sequence of bases in the template strand. Template dependent primer extension reactions include both amplification and non-amplification primer extension reactions. In some embodiments of the subject invention, the template dependent primer extension reaction in which the production of primer extension products is detected is an amplification reaction, e.g. a polymerase chain reaction (PCR).

In the present invention the template dependent primer extension reaction in which the production of primer extension products is detected is a reaction containing primers modified with phosphorothioate groups in conjunction with polymerases lacking 3'→5' nuclease activity.

In practicing the methods of the invention, the first step is to produce a primer extension mixture, e.g. a composition that includes all of the elements necessary for primer extension reaction to occur. For example the primer extension mixture may include at least two single-labelled oligonucleotide sequences, e.g. of differing Tm, that hybridise to one another in free solution to form a fluorescent quenched pair and that upon introduction of a complementary sequence to one or both sequences generates a measurable signal, wherein one of the sequences for example has a Tm that is at or below the Ta, (a "FET cassette primer pair"), wherein at least one of the oligonucleotide sequences contains at least one phosphorothioate group.

FET occurs when a suitable fluorescent energy donor and an energy acceptor moiety are in close proximity to one another. The excitation energy absorbed by the donor is transferred to the acceptor which can then further dissipate this energy either by fluorescent emission if a fluorophore, or by non-fluorescent means if a quencher. A donor-acceptor pair comprises two fluorophores having overlapping spectra, where the donor emission overlaps the acceptor absorption, so that there is energy transfer from the excited fluorophore to the other member of the pair. It is not essential that the excited fluorophore actually fluoresce, it being sufficient that the excited fluorophore be able to efficiently absorb the excitation energy and efficiently transfer it to the emitting fluorophore. As such, the FET cassette(s) employed in the subject methods are nucleic acid detectors that include on separate oligonucleotides a fluorophore domain where the fluorescent energy donor, i.e. donor, is positioned and a second oligonucleotide with an acceptor domain where the fluorescent energy acceptor, i.e. acceptor, is positioned. As mentioned above, the donor oligonucleotide includes the donor fluorophore. The donor fluorophore may be positioned anywhere in the nucleic acid detector, but is typically present at the 5' terminus of the detector.

The acceptor domain includes the fluorescence energy acceptor. The acceptor may be positioned anywhere in the acceptor domain, but is typically present at the 3' terminus of the nucleic acid detector.

In addition to the fluorophore and acceptor domains, the FET cassette acceptor oligonucleotides also include a target nucleic acid binding domain, which binds to a target nucleic acid sequence which is created from the non-labelled tailed primers included in the reaction, e.g. under stringent hybridization conditions (as defined below).

Depending on the nature of the oligonucleotide and the assay itself, the target binding domain may hybridize to a region of the primer extension product. For example, where the assay is a SNP genotyping assay, e.g. in which a universal cassette reporting system is employed, the target binding domain hybridizes under stringent conditions to a target binding site of primer extension product. The fluorophores for FET oligonucleotide pairs may be selected so as to be from a similar chemical family or a different one, such as cyanine dyes, xanthenes or the like. Fluorophores of interest include, but are not limited to fluorescein dyes (e.g. 5-carboxyfluorescein (5-FAM), 6-carboxyfluorescein (6-FAM), 2',4',1,4,-tetrachlorofluorescein (TET), 2',4',5',7', 1,4-hexachlorofluorescein (HEX), and 2',7'-dimethoxy-4',5'-dichloro-6-carboxyfluorescein (JOE)), cyanine dyes such as Cy5, dansyl derivatives, rhodamine dyes (e.g. tetramethyl-6-carboxyrhodamine (TAMRA), and tetrapropano-6-carboxyrhodamine (ROX)), DABSYL, DABCYL, cyanine, such as Cy3, anthraquinone, nitrothiazole, and nitroimidazole compounds, and the like. Fluorophores of interest are further described in International Patent Applications WO 01/42505 and WO 01/86001.

Since the primer extension reaction mixture produced in the initial step of the subject methods is a 3'→5' exonuclease deficient primer extension reaction mixture, it further includes an enzyme having no 3'→5' exonuclease activity. In many embodiments, the polymerase combination employed includes at least one Family A, where the terms "Family A" and "Family B" correspond to the classification scheme reported in Braithwaite & Ito, Nucleic Acids Res. (1993) 21:787-802. Family A polymerases of interest include: *Thermus aquaticus* polymerases, including the naturally occurring polymerase (Taq) and derivatives and homologues thereof, such as Klentaq (as described in Proc. Natl. Acad. Sci USA (1994) 91:2216-2220); *Thermus thermophilus* polymerases, including the naturally occurring polymerase (Tth) and derivatives and homologues thereof, and the like. The polymerase for use in the invention may be used in purified or unpurified form.

Another component of the reaction mixture produced in the first step of the methods is the template nucleic acid. The nucleic acid that serves as template may be single stranded or double stranded, where the nucleic acid is typically deoxyribonucleic acid (DNA). The length of the template nucleic acid may be as short as 50 bp, but usually be at least about 100 bp long, and more usually at least about 150 bp long, and may be as long as 10,000 bp or longer, e.g. 50,000 bp in length or longer, including a genomic DNA extract, or digest thereof, etc. The nucleic acid may be free in solution, flanked at one or both ends with non-template nucleic acid, present in a vector, e.g. plasmid and the like, with the only criteria being that the nucleic acid be available for participation in the primer extension reaction. The template nucleic acid may be present in purified form, or in a complex mixture with other non-template nucleic acids, e.g. in cellular DNA preparation, etc.

The template nucleic acid may be derived from a variety of different sources, depending on the application for which the PCR is being performed, where such sources include organisms that comprise nucleic acids, i.e. viruses; prokaryotes, e.g. bacteria, archaea and cyanobacteria; and eukaryotes, e.g. members of the kingdom protista, such as flagellates, amoebas and their relatives, amoeboid parasites, ciliates and the like; members of the kingdom fungi, such as slime molds, acellular slime molds, cellular slime molds, water molds, true molds, conjugating fungi, sac fungi, club fungi, imperfect fungi and the like; plants, such as algae, mosses, liverworts, hornworts, club mosses, horsetails, ferns, gymnosperms and flowering plants, both monocots and dicots; and animals, including sponges, members of the phylum cnidaria, e.g. jelly fish, corals and the like, comb-jellies, worms, rotifers, roundworms, annelids, molluscs, arthropods, echinoderms, acorn worms, and vertebrates, including reptiles, fishes, birds, snakes, and mammals, e.g. rodents, primates, including humans, and the like. The template nucleic acid may be used directly from its naturally occurring source and/or preprocessed in a number of different ways, as is known in the art. In some embodiments, the template nucleic acid may be from a synthetic source.

The next component of the reaction mixture produced in the first step of the subject methods is the primers employed in the primer extension reaction, e.g. the PCR primers (such as forward and reverse primers employed in geometric amplification or a single primer employed in a linear amplification). Each primer extension reaction mix will comprise at least two primers (in the case of linear amplification) and usually three primers and more usually five or seven primers in the case of a SNP genotyping reaction. A primer extension reaction mix will comprise at least a fluorescently donor labelled primer and a complimentary acceptor, quencher labelled primer in the case of linear amplification where one or both of the primers will contain at least one phosphorothioate group.

More usually in the case of exponential amplification the primer extension mix will comprise at least a fluorescently donor labelled primer and a complimentary acceptor, quencher labelled primer, and a reverse unlabelled primer, where one of or any of the primers will contain at least one phosphorothioate group. Most usually, in the case of exponential amplification using a universal reporter system the primer extension mix will comprise at least a fluorescently acceptor labelled primer and a complimentary donor, quencher labelled primer, a reverse unlabelled primer and a tailed forward primer, where one of or any of the primers will contain at least one phosphorothioate modification. The oligonucleotide primers with which the template nucleic acid (hereinafter referred to as template DNA for convenience) is contacted will be of sufficient length to provide for hybridization to complementary template DNA under annealing conditions (described in greater detail below) but will be of insufficient length to form stable hybrids with template DNA under polymerization conditions. The primers may be at least 10 bp in length, e.g. at least 15 bp or 16 bp in length. Primers may be 30 bp in length or longer, for example, the length of the primers may be 18 to 60 bp in length, such as from about 20 to 35 bp in length. The template DNA may be contacted with a single primer or a set of two primers (forward and reverse primers), depending on whether primer extension, linear or exponential amplification of the template DNA is desired. Where a single primer is employed, the primer will typically be complementary to one of the 3' ends of the template DNA and when two primers are employed, the primers will typically be complementary to the two 3' ends of the double stranded template DNA.

As used herein, "nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and functionality to the nucleic acid. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

As used herein, "complimentary" refers to the pair of nitrogenous bases, consisting of a purine linked by hydrogen bonds to a pyrimidine, that connects the complementary strands of DNA or of hybrid molecules joining DNA and RNA.

As used herein, "fluorescent group" refers to a molecule that, when excited with light having a selected wavelength, emits light of a different wavelength. Fluorescent groups may also be referred to as "fluorophores".

As used herein, "fluorescence-modifying group" refers to a molecule that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, a change in fluorescence lifetime. One example of a fluorescence-modifying group is a quenching group.

As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. Energy transfer is also referred to herein as fluorescent energy transfer or FET.

As used herein, "energy transfer pair" refers to any two molecules that participate in energy transfer. Typically, one of the molecules acts as a fluorescent group, and the other acts as a fluorescence-modifying group. The preferred energy transfer pair of the instant invention comprises a fluorescent group and a quenching group. In some cases, the distinction between the fluorescent group and the fluorescence-modifying group may be blurred. For example, under certain circumstances, two adjacent fluorescein groups can quench one another's fluorescence emission via direct energy transfer. For this reason, there is no limitation on the identity of the individual members of the energy transfer pair in this application. All that is required is that the spectroscopic properties of the energy transfer pair as a whole change in some measurable way if the distance between the individual members is altered by some critical amount.

"Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another.

As used herein, "primer" refers to an oligonucleotide which is capable of acting as a point of initiation of synthesis when placed under conditions in which synthesis of a primer extension product which is complementary to a nucleic acid strand are induced (e.g. under stringent hybridization conditions). The term "oligonucleotide sequence" may be used herein to refer to a primer and vice versa.

As used herein, "quenching group" refers to any fluorescence-modifying group that can attenuate at least partly the light emitted by a fluorescent group. We refer herein to this attenuation as "quenching". Hence, illumination of the fluorescent group in the presence of the quenching group leads to an emission signal that is less intense than expected, or even completely absent. Quenching occurs through energy transfer between the fluorescent group and the quenching group.

As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly.

As used herein "tailed primer" refers to an oligonucleotide containing two domains, one specific to the target template DNA of interest and the other a unique sequence serving as a template for production of product from universal primers present in every different and distinct PCR reaction.

As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others electronic structure. If the fluorescence-modifying group is a quenching group, this will result in the quenching group preventing the fluorescent group from even emitting light.

In general, quenching by direct energy transfer is more efficient than quenching by FRET. Indeed, some quenching groups that do not quench particular fluorescent groups by FRET (because they do not have the necessary spectral overlap with the fluorescent group) can do so efficiently by direct energy transfer. Furthermore, some fluorescent groups can act as quenching groups themselves if they are close enough to other fluorescent groups to cause direct energy transfer. For example, under these conditions, two adjacent fluorescein groups can quench one another's fluorescence effectively. For these reasons, there is no limitation on the nature of the fluorescent groups and quenching groups useful for the practice of this invention.

An example of "stringent hybridization conditions" is hybridization at 50° C. or higher and 6.0*SSC (900 mM NaCl/90 mM sodium citrate). Another example of stringent hybridization conditions is overnight incubation at 42° C. or higher in a solution: 50% formamide, 6*SSC (900 mM NaCl, 90 mM trisodium citrate), 50 mM sodium phosphate (pH 7.6), 10% dextran sulfate, and 20 ug/ml denatured, sheared salmon sperm DNA. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed.

References to sequences being identical herein may be interpreted to mean sequences that are identical or substantially homologous to one another.

Examples of the use of the present invention include the following:

Direct Detection of PCR Products:

This embodiment, illustrated in FIG. 1 A-E, utilises an oligonucleotide primer to initiate the PCR process. This conventional primer is directed to the template region of interest and therefore drives the specificity of the reaction. This oligonucleotide is also fluorescently-labelled at the 5' end. A number of suitable fluorophores exist, with a popular choice being FAM (a derivative of fluorescein). Finally, included in the reaction is a 3' quencher-labelled oligonucleotide antisense to the FAM labelled oligonucleotide. A number of suitable labels exist of which the Black Hole quencher series of labels are a popular choice. Provided the length of the quencher oligonucleotide is long enough to give a Tm above the Ta of the reaction the product generation can be assessed at each cycle of the PCR process on any real-time PCR instrument (such as a ABI 7900 Prism instrument) Alternatively the reaction may employ a quenching oligonucleotide that has a Tm lower than the Ta of the reaction. Post PCR the reaction is cooled to room temperature and the products may be assessed on any such real-time instrument and in addition any fluorescent plate reader (such as a BMG Pherastar).

Due to the complementarity of the two-labelled oligonucleotides (quencher and fluorophore labelled), they hybridise to each other. This hybridisation brings the quencher label in very close proximity to the fluorophore, thereby rendering all fluorescent signal from the FAM molecule quenched, when excited at 488 nm (the optimal excitation wavelength of FAM).

Also included in the reaction is a conventional reverse primer to create a PCR primer pair. The PCR process is then initiated and PCR product begins to be generated.

After the first few cycles of PCR the antisense sequence to the fluorescent primer is generated. During this process the quencher oligonucleotide no longer binds; this produces amplicon containing a 5' FAM molecule. Once this occurs the quenching oligo is no longer able to hybridise to the FAM-labelled oligonucleotide, as the PCR process produces double-stranded amplicon DNA. As the quenching oligonucleotide can no longer hybridise to the FAM oligonucleotide, signal is then generated which is directly proportional to the amount of PCR product generated.

Summary of the steps in the reaction schema of FIG. 1 A-E are given below:
1. Reaction components Taq DNA polymerase
   deoxynucleotide triphosphates dNTPs
   Reaction Buffer
2. 1st round of thermal cycling—forward tailed primer hybridises to genomic DNA and quencher oligonucleotide is hybridised to fluorophore-labelled tail portion of the oligonucleotide. Reverse primer hybridises to genomic DNA (not shown).
3. DNA synthesis occurs copying genomic DNA incorporating the tail sequence into the synthesized strand.
4. Synthesised strand DNA is copied inclusive of primer tail. Reverse strand is also primed and copied from more tailed primer (not shown).
5. DNA synthesis is initiated from fluorescent labelled primer.

Indirect (Real-Time) Detection of PCR Products

This embodiment, illustrated in FIG. 2 A-E, utilises a conventional oligonucleotide (primer) to initiate the PCR process. This conventional primer is tailed with a DNA sequence that is not directed to the amplicon region of interest, whereby this tail is essentially inert. This tail sequence is positioned at the 5' portion of the primer. Also included in the reaction is a single fluorescently-labelled oligonucleotide that is identical to or substantially homologous to the tail sequence region of the conventional primer. A number of suitable fluorophores exist, with a popular choice being FAM (a derivative of fluorescein). Finally, included in the reaction is a 3' quencher-labelled oligonucleotide antisense to the FAM labelled oligonucleotide. A number of suitable labels exist of which the Black Hole quencher series of labels are a popular choice.

Provided the length of the quencher oligonucleotide is long enough to give a Tm above the Ta of the reaction the product generation can be assessed at each cycle of the PCR process on any real-time PCR instrument (such as a ABI 7900 Prism instrument). Alternatively the reaction may employ a quenching oligonucleotide that has a Tm lower than the Ta of the reaction. Post PCR the reaction is cooled to room temperature and the products may be assessed on any such real-time instrument and in addition any fluorescent plate reader (such as a BMG Pherastar).

Due to the complementarity of the two labelled oligonucleotides, they hybridise to each other. This hybridisation brings the quencher label in very close proximity to the fluorophore, thereby rendering all fluorescent signal from the FAM molecule quenched, when excited at 488 nm (the optimal excitation wavelength of FAM). The PCR process is then initiated and PCR product begins to be generated. After the first few cycles of PCR the antisense sequence to the fluorescent primer is generated. The fluorescent PCR primer is then able to initiate synthesis during the PCR, and does so. This produces amplicon containing a 5' FAM molecule. Once this occurs the quenching oligo is no longer able to hybridise to the FAM-labelled oligonucleotide, as the PCR process produces double-stranded amplicon DNA. As the quenching oligonucleotide can no longer hybridise to the FAM oligonucleotide, signal is then generated which is directly proportional to the amount of PCR product generated.

The tail region of the tailed primer need not be identical to the single fluorescently-labelled oligonucleotide, as long as an antisense sequence of the trail region generated hybridises to the single fluorescently-labeled oligonucleotide.

Summary of the steps in the reaction schema of FIG. 2 A-E are given below:
1. Reaction components Taq DNA polymerase
   deoxy nucleotides triphosphates dNTPs
   Reaction Buffer
2. 1st round of thermal cycling—the forward, tailed primer hybridises to genomic DNA and the quencher oligonucleotide hybridises to its complementary fluorophore-labelled oligonucleotide. The reverse primer hybridises to genomic DNA (not shown).
3. DNA synthesis occurs from the oligonucleotide copying genomic DNA incorporating the x tail sequence into the synthesised strand. The reverse strand is not shown.
4. Synthesised strand DNA is copied inclusive of primer tails. Reverse strand is also primed and copied from more tailed primer (not shown).
5. DNA synthesis is initiated from x-fluorescently-labelled primer.

Indirect (End-Point) Detection of PCR Products—SNP Genotyping:

This embodiment, illustrated in FIG. 3 A-E, utilises the same fluorophore- and quencher-labelled oligonucleotide pair as described in FIG. 2 A-E. The reaction schema is identical but for a few modifications.

To achieve SNP genotyping requires the use of two fluorescently-labelled primers and corresponding quencher-labelled oligonucleotides. Each primer is again tailed with a unique sequence, to which in the reaction is included a 5' fluorescently-labelled primer. Two suitable dyes are FAM and HEX, which are spectrally-resolvable from each other. The two primers (non-tailed portion; generally termed forward) are directed to the DNA of interest. In this portion of the primer they typically differ only by a single nucleotide at their 3' terminal base. Each primer is directed to the polymorphic base in the DNA of interest. PCR is conducted and the two primers only initiate synthesis when the 3' base is perfectly matched. When a mismatch occurs synthesis does not proceed.

During the reaction, the specific tail depending on the genotype is able to initiate synthesis (or both are, in the case of a heterozygote). This again incorporates the fluorescent tail portion of the primer in to the PCR product thereby hindering the hybridisation of the quencher oligonucleotide. Signal is therefore generated according to which of the oligonucleotides has initiated the synthesis. The reaction is then read on a fluorescent plate-reader for both fluorophores. Their resulting data is then plotted and a cluster plot of one fluorophore over the other is generated. The resulting genotypes are then able to be determined based on the cluster plots.

Summary of the steps of the reaction schema of FIG. 3 A-E are given below:
1. Reaction components Taq DNA polymerase
    deoxy nucleotides triphosphates dNTPs
    Reaction Buffer
2. 1st round of thermal cycling-depending on genotype of DNA under test either or both forward tailed primer hybridise to genomic DNA and quencher oligonucleotides are hybridised to their complementary fluorophore labelled oligonucleotide. Reverse primer hybridises to genomic DNA (not shown). Example shows heterozygous individual.
3. DNA synthesis occurs from both allele-specific oligonucleotides copying genomic DNA incorporating the x and y tail sequences into the synthesised strands. The reverse strand is not shown.
4. Synthesised strand DNA is copied inclusive of primer tails. Reverse strand is also primed and copied from more tailed allele specific primer (not shown).
5. DNA synthesis is initiated from both x and y fluorescent labelled primers.

A further use of the fluorophore quencher pair oligo system described is in the homogeneous detection of PCR products with the use of 5'-3' nuclease activity of Taq polymerase.

The current invention can be employed to improve upon the specificity and primer dimer formation that also occurs in the 5' nuclease assay, otherwise know as taqman.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein are incorporated herein by reference to the fullest extent possible for the purpose of describing and disclosing those components that are described in the publications which might be used in connection with the presently described invention.

The invention will now be described by reference to the following examples which are for illustrative purposes and are not to be construed as a limitation of the scope of the present invention.

Example 1

Abbreviations:
FAM: 6-Carboxy Fluorescein
HEX: 2',4',5',7',1,4-hexachlorofluorescein
Dabcyl: non-fluorescent dark quencher Seven oligonucleotides were designed and their sequences can be found below, where * denotes use of S-modification:

1) Semi S FAM fluorescently-labelled oligonucleotide:
(SEQ ID NO: 3)
5'-FAM-G*CG*AT*TA*GC*CG*TT*AG*GA*TG*A3'

2) Semi S HEX fluorescently-labelled oligonucleotide:
(SEQ ID NO: 7)
5'-HEX-G*TC*GG*TG*AA*CA*GG*TT*AG*AG*A3'

3) Standard FAM Quencher:
(SEQ ID NO: 9)
5' CCTAACGGCTAATCGC-3' Dabsyl

4) Standard HEX Quencher:
(SEQ ID NO: 13)
5' AACCTGTTCACCGAC-3' Dabsyl

5) Allele specific primer 1:
(SEQ ID NO: 17)
5' GCGATTAGCCGTTAGGATGACTGAGTGCAGGTTCAGACGTCC 3'

6) Allele specific primer 2:
(SEQ ID NO: 18)
5' GTCGGTGAACAGGTTAGAGACTGAGTGCAGGTTCAGACGTCT 3'

7) Common reverse primer:
(SEQ ID NO: 19)
5' CTCCCTTCCACCTCCGTACCAT 3'

It will be noted that in this example the FAM-labelled quenching primer has a 16mer oligonucleotide sequence and is more than 2 nucleotides shorter than the FAM-labelled primer/reporter probe and similarly the HEX-labelled quenching primer has a 15mer oligonucleotide sequence and is more than 2 nucleotides shorter than the HEX-labelled primer/reporter probe. Accordingly, the longer FAM- or HEX-labelled primers/reporter probes have a Tm that is at or above the 57° C. Ta of the annealing step of the PCR process and will anneal with the template in the process, whereas the shorter quenching primers are at or below the 57° C. Ta of the annealing step and will not anneal with the template.

All oligonucleotides were diluted to 200 μM initial concentrations in 10 mM Tris/HCl pH 8.0. All further dilutions were carried out in this diluent. An assay mix was created which included the following components:
(1) 0.16 uM Allele-specific primer 1
(2) 0.16 uM Allele-specific primer 2
(3) 0.41 uM Reverse (common) primer
(4) 0.1 uM FAM-labelled oligonucleotide
(5) 0.1 uM HEX-labelled oligonucleotide
(6) 0.5 uM Quencher-labelled oligonucleotide (antisense to oligonucleotide 4)
(7) 0.5 uM Quencher-labelled oligonucleotide (antisense to oligonucleotide 5)
(8) 30-90 Units/mL N-terminal truncated Taq polymerase
(9) 10 mM Tris/HCl pH 8.3
(10) 10 mM KCl
(11) 1.8 mM Magnesium chloride
(12) 165.2 uM dNTPs
(13) 212.5 nM 5-carboxy-X-rhodamine, SE (5-ROX, SE)

To wells A1-B24 of a 384 well microtitre plate 10 ng of genomic DNA was added from 44 Caucasian individuals. The remaining 4 wells were left empty serving as negative control wells. This plate was then dried at 50° C. for a period of 1 hour.

To wells A1-B24 of the dried plate 5 μL of assay mix was added and the plate sealed using a Fusion transmission diode laser plate sealer (KBioscience UK Ltd). The plate was then thermal-cycled under the following conditions in a Hydrocycler (KBioscience UK Ltd):

(1) 94° C. for 15 minutes hot-start activation
(2) 94° C. for 20 seconds
(3) 61-55° C. for 60 seconds (dropping 0.8° C. per cycle)
10 cycles of the above
(4) 94° C. for 20 seconds
(5) 55° C. for 60 seconds
26 cycles of the above Post thermal-cycling the fluorescence associated with each well was determined using a BMG Pherastar plate reader. Each well was read three times at the following wavelength combinations.

FAM excitation: 485 nm, FAM emission: 520 nm
HEX excitation: 535 nm, HEX emission: 556 nm
ROX excitation: 575 nm, ROX emission: 610 nm The resulting data was then plotted as FAM signal divided by ROX on the X axis, and HEX signal divided by ROX on the Y axis.

Figure 4:
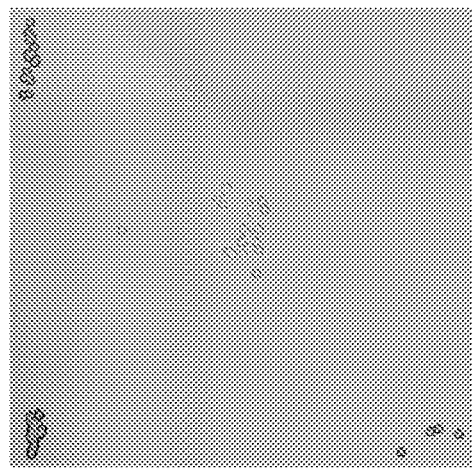
FIG. 4 shows data generated using the assay described in Example 1 below.

As can be seen from the resulting scatter plot of FIG. 4, three clearly discernible groups associated with the respective genotypes are visible clearly demonstrating the effectiveness of the detection technology.

Example 2

Following a protocol similar to that described in Example 1, assays were conducted to compare the use of fluorescently-labelled oligonucleotides of the (i) non-S modified, (ii) semi-S modified (alternate phosphorothioates) and (iii) full-S modified configurations. The data generated is presented in FIG. 5 A-E. The data shown for Assay 1 demonstrates the use configurations (i), (ii) and (iii) (above); the data for Assay 2 demonstrates configurations (i) and (ii). In both assays the quencher oligonucleotides had no phosphorothioate modification.

FIG. 5 A-E shows differently modified fluorescent oligos with standard (non-S modified) quenchers.

Figure 5A:
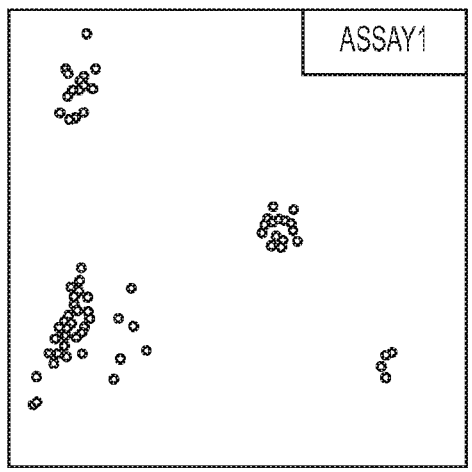
FIG. 5 A-E shows a comparison of data generated in assay systems using oligonucleotide sequences containing phosphorothioate groups and non-phosphorothioate containing oligonucleotides as described in Example 2 below.

FIG. 5A shows standard (non-phosphorothioate modified) fluorescently-labelled primers.

Figure 5B:
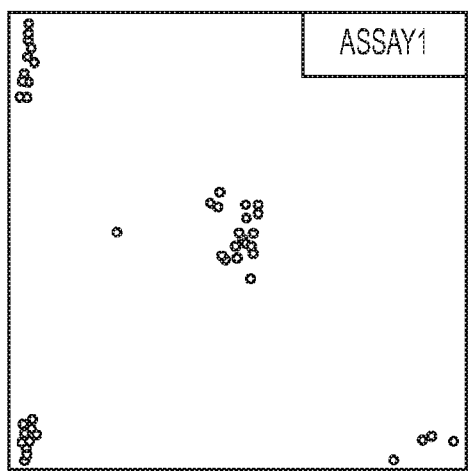

FIG. 5B shows semi-S phosphorothioate-modified fluorescently-labelled primers.

Figure 5C:
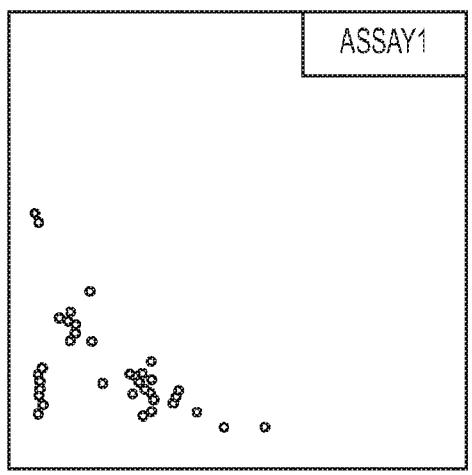

FIG. 5C shows full-S phosphorothioate-modified fluorescently-labelled primers.

Figure 5D:
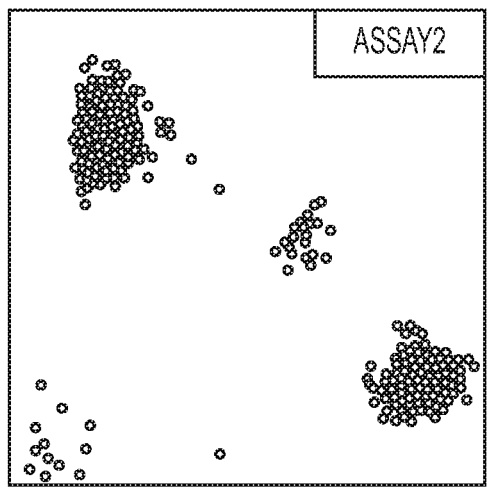

FIG. 5D shows standard (non-phosphorothioate modified) fluorescently-labelled primers.

Figure 5E:
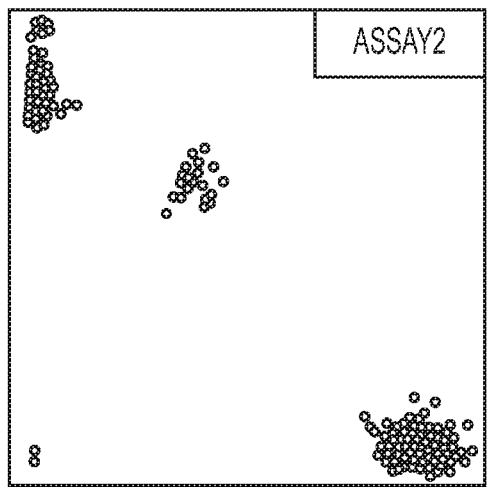

FIG. 5E shows semi-S phosphorothioate-modified fluorescently-labelled primers.

Enhanced specificity and reduced no-template control amplification (see bottom left hand scatter plot) was observed with all the variants of phosphorothioate modified fluors. The use of phosphosphorothioate modification on all the bases of the fluorescently-labelled oligonucleotide had some effect on the PCR speed and the signal intensity. Use of phosphorothioate modification on alternate bases of the fluor-labelled primers (referred to as semi-S modification) in conjunction with unmodified quenchers were found to be optimal for enhanced discrimination and signal intensity of the PCR and hence this represents the preferred embodiment of the invention.

The invention claimed is:

1. A kit for the detection of a primer extension product produced in the presence of a polymerase lacking 3'→5' exonuclease activity, that comprises:
   1) at least two single-labelled oligonucleotide sequences that hybridize to one another in free solution to form a fluorescent quenched pair, that upon introduction of a complementary sequence to one or both sequences generates a measurable signal when the complementary sequence is hybridized to one of the at least two single-labelled oligonucleotide sequences; and
   2) a polymerase lacking 3'→5' exonuclease activity;
   wherein at least one of the internal bases of at least one of the oligonucleotide sequences is modified by a phosphorothioate group and wherein:
   the at least one oligonucleotide sequence that contains at least one phosphorothioate group has 20-80% of the bases modified by a phosphorothioate group.

2. The kit according to claim 1, wherein the first and second oligonucleotide sequences are of different melting temperature Tm.

3. The kit according to claim 2 wherein the kit is suitable for use in a method for the detection of a primer extension product produced in the presence of a polymerase lacking 3'→5' exonuclease activity, the method comprising the steps of:

(a) providing the at least two single-labelled oligonucleotide sequences that hybridize to one another in free solution to form a fluorescent quenched pair as defined in claim 1;
   (b) providing at least one primer and a polymerase lacking 3'→5' exonuclease activity and initiating the primer extension reaction from the at least one primer, thereby generating a complementary sequence to at least one of the single-labelled oligonucleotide sequences; and
   (c) measuring a detectable signal that is generated when the complementary sequence is hybridized to one of the at least two single-labelled oligonucleotide sequences.

4. The kit according to claim 3, wherein one of the first and second oligonucleotide sequences has a melting temperature Tm that is at or below the annealing temperature Ta of the primer extension reaction.

5. The kit according to claim 3, wherein one of the first and second oligonucleotide sequences has a melting temperature Tm that is above the annealing temperature Ta of the primer extension reaction.

6. The kit according to claim 4, wherein the at least one primer comprises at least one unlabelled tailed primer, the unlabelled tailed primer having a tail region, the tail region comprising an oligonucleotide sequence complementary to an oligonucleotide sequence of the second single-labelled oligonucleotide sequence, the first single-labelled oligonucleotide sequence being a primer from which DNA synthesis is initiated once a complementary sequence to the first single-labelled oligonucleotide sequence has been generated during the primer extension reaction, such that the second single-labelled oligonucleotide sequence is no longer able to hybridize to the first single-labelled oligonucleotide sequence, whereby a measurable signal is generated.

7. A kit according to claim 1, wherein one of the single-labelled oligonucleotides is more than 10 bases shorter than the other.

8. A kit according to claim 3, wherein the primer extension reaction is monitored in real time at each cycle or after a number of cycles where the reaction has otherwise not yet generated enough product to create a measurable signal by lowering the temperature of the reaction to allow hybridization to occur.

9. A kit according to claim 6, wherein said other of the single-labelled oligonucleotides has a melting temperature Tm that is above the annealing temperature Ta.

10. A kit according to claim 1, wherein said one of the single-labelled oligonucleotides has a quencher label of the fluorescent quenched pair.

11. A kit according to claim 1 wherein 20-80% of the bases of phosphorothioate group-containing oligonucleotide sequences are phosphorothioates.

12. A kit according to claim 1, wherein the fluorescent quench oligo pairs range from 6 bp to 100 bp.

13. A kit according to claim 12 wherein the fluorescent quench oligo pairs range from 6 bp to 100 bp but are not matched in length.

14. A kit according to claim 1 wherein at least one of the bases of a fluorophore-labelled oligonucleotide sequence contains at least one phosphorothioate group.

15. A kit according to claim 1, wherein one of the fluorescent quenched pairs is labelled with a fluorophore and the other is labelled with a non fluorescent quenching molecule.

16. A kit according to claim 1, wherein the fluorescent quench oligo pairs are modified to be resistant to nuclease degradation.

17. A kit according to claim 1, wherein the fluorescent quench oligo pairs are labelled with molecules that are distance sensitive.

18. A kit according to claim 1, wherein the modified bases of the at least one oligonucleotide sequence that contains at least one phosphorothioate group are separated by at least one unmodified base.

19. A kit according to claim 1, wherein the at least one oligonucleotide sequence that contains at least one phosphorothioate group has alternate phosphorothioate bases.

* * * * *